United States Patent
Herrmann

(10) Patent No.: US 6,492,323 B2
(45) Date of Patent: *Dec. 10, 2002

(54) SLOW RELEASE OF FRAGRANT COMPOUNDS IN PERFUMERY USING α-KETO ESTERS

(75) Inventor: Andreas Herrmann, Geneva (CH)

(73) Assignee: Firmenich SA, Geneva (CH)

( * ) Notice: Subject to any disclaimer, the term of this patent is extended or adjusted under 35 U.S.C. 154(b) by 10 days.

This patent is subject to a terminal disclaimer.

(21) Appl. No.: 09/794,694

(22) Filed: Feb. 27, 2001

(65) Prior Publication Data

US 2001/0014661 A1 Aug. 16, 2001

Related U.S. Application Data

(60) Division of application No. 09/316,390, filed on May 21, 1999, now Pat. No. 6,218,355, which is a continuation-in-part of application No. 09/085,593, filed on May 28, 1998, now Pat. No. 6,133,228.

(51) Int. Cl.⁷ .............................. A61K 7/46; A61L 9/04
(52) U.S. Cl. ................. 512/27; 512/2; 512/25; 512/26; 560/129
(58) Field of Search ................. 512/27, 2, 25, 512/26; 560/129

(56) References Cited

U.S. PATENT DOCUMENTS

| | | | |
|---|---|---|---|
| 3,903,064 A | 9/1975 | Isigami et al. | 260/87.3 |
| 3,926,640 A | 12/1975 | Rosen | 96/115 P |
| 3,926,641 A | 12/1975 | Rosen | 96/115 P |
| 4,080,275 A | 3/1978 | Photis et al. | 204/159.23 |
| 4,180,674 A | 12/1979 | Photis | 560/52 |
| 4,781,914 A | 11/1988 | Deckner | 424/59 |
| 4,981,973 A | 1/1991 | Murray | 548/229 |
| 5,032,382 A | 7/1991 | Grollier et al. | 424/47 |
| 6,218,355 B1 * | 4/2001 | Herrmann | 424/76.4 |

FOREIGN PATENT DOCUMENTS

JP    06 121 822    5/1994

OTHER PUBLICATIONS

Hu, Shengkui et al., "Photochemical Reactions of Alkenyl Phenylglyoxylates", *Journal of Organic Chemistry*, 62(20):6820–6826 (1997).

Klimova, E.I. et al., in *Chemical Abstracts*, 112 473d, vol. 71, No. 23 (1969).

Kraus, George A., et al., "1,5 and 1,9–Hydrogen Atom Abstractions, Photochemical Strategies for Radical Cyclizations", *Journal of the American Chemical Society*, 114(22):8705–8707 (1992).

Jones et al., "Benzoylbenzoic Acid: A Photolabile Mask for Alcohols and Thiols", *Journal of Organic Chemistry*, 61:9455–9461 (1996).

\* cited by examiner

*Primary Examiner*—Jill Warden
*Assistant Examiner*—Monique T. Cole
(74) *Attorney, Agent, or Firm*—Winston & Strawn

(57) ABSTRACT

The present invention describes a fragrance delivery system which releases fragrant aldehydes or ketones and/or fragrant compounds containing an olefin function upon exposure to light. This system comprises α-keto esters of formula

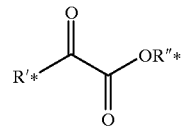

in which R'* and R"* have the meaning as defined in the application and which are generally, in case of R'*, an alkyl group carrying an abstractable hydrogen in γ-position relative to the α-keto function and carrying a moiety from which is derived a fragrant compound containing an olefin function, and, in case of R"*, the organic part of a primary or secondary alcohol from R"*OH which is derived a fragrant aldehyde or ketone.

2 Claims, No Drawings

SLOW RELEASE OF FRAGRANT COMPOUNDS IN PERFUMERY USING α-KETO ESTERS

This application is a division of application Ser. No. 09/316,390, filed May 21, 1999, now U.S Pat. No. 6,218,355, which is a continuation-in-part of application Ser. No. 09/085,593, filed May 28, 1998, now U.S. Pat. No. 6,133,228.

BRIEF SUMMARY OF THE INVENTION

The present invention describes a fragrance delivery system which releases fragrant aldehydes or ketones and/or fragrant compounds containing an olefin function upon exposure to light. This system comprises α-keto esters of formula

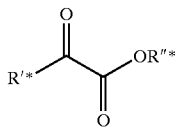

in which R'* and R"* have the meaning as defined in the application and which are generally, in case of R'*, an alkyl group carrying an abstractable hydrogen in γ-position relative to the α-keto function and carrying a moiety from which is derived a fragrant compound containing an olefin function, and, in case of R"*, the organic part of a primary or secondary alcohol from R"*OH which is derived a fragrant aldehyde or ketone.

BACKGROUND OF THE INVENTION

The present invention relates to the field of perfumery. It relates, more particularly, to α-keto esters, as defined below, of alcohols which are precursors of fragrant aldehydes and ketones and which are capable of releasing said fragrant ketone or aldehyde upon exposure to light, more particularly daylight. Said α-keto esters may furthermore contain, in α-position to the keto group, an alkyl group which may contain various substituents and which alkyl group is derived from a fragrant molecule possessing an olefinic unsaturation. The unsaturated molecule and/or the aldehyde or ketone are released upon exposure to light, in particular daylight, of the α-keto ester.

There exists, in perfumery, a particular interest in compounds which are capable of "fixing" fragrant molecules, for example by chemical bonding or intramolecular forces like absorption, and releasing said fragrant molecules over a prolonged period of time, for example by the action of heat, enzymes, or even sunlight. Fragrant molecules have to be volatile in order to be perceived. Although many fragrant compounds are known which show a good substantivity, i.e. they will remain on a surface to which they have been applied for several days and can hence be perceived over such a period of time, a great number of fragrant compounds are very volatile, and their characteristic smell can no longer be perceived several hours after their application.

It is thus desirable to dispose of fragrance delivery systems which are capable of releasing the fragrant compound or compounds in a controlled manner, maintaining a desired smell over a prolonged period of time.

DETAILED DESCRIPTION OF THE INVENTION

We have now developed a fragrance delivery system which is capable of releasing fragrant aldehydes or ketones and/or fragrant compounds containing an olefin function upon exposure to light, and in particular daylight.

The object of the present invention is a fragrance delivery system comprising α-keto esters of formula

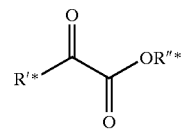

in which
- R'* is hydrogen or a linear or branched, unsubstituted or substituted alkyl group or alkylene group from $C_1$ to $C_{35}$, an unsubstituted or substituted cycloalkyl group from $C_3$ to $C_8$, an unsubstituted or substituted phenyl group, wherein said alkyl, alkylene, cycloalkyl and phenyl groups may comprise one or several hetero atoms not directly linked to the α-keto group and selected from the group consisting of oxygen, nitrogen, phosphorous and sulfur, or
- R'* is a substituted or unsubstituted, linear or branched alkyl group carrying an abstractable hydrogen in γ-position relative to the α-keto function and comprising a moiety from which is derived a fragrant compound containing an olefin function, such that said fragrant compound containing an olefin function is eliminated after abstraction of said γ-hydrogen atom;
- R"* is hydrogen or a methyl, ethyl or tert-butyl group or is the organic part of a primary or secondary alcohol from which is derived a fragrant aldehyde or ketone, and at least one of the groups R'* and R"* being a group which is derived from a fragrant compound.

Many of the α-keto ester compounds of the above formula are new. Certain compounds are not, however, such as those of the above formula when R'* is a methyl group, or when R"* is a menthyl or a benzyl group. Specifically, (−)-(1S,1R)-1,7,7-trimethylbicyclo[2.2.1]heptan-2-yl (4-methylphenyl)oxoacetate and hexyl(cyclohexyl) oxoacetate are excluded.

In the above definition, when reference is made to a fragrant compound, aldehyde or ketone, it is always meant a compound which not only has an odor, but which is also known to a person skilled in the art as being useful as a perfuming ingredient for the formulation of perfumes or perfumed articles. The criteria a useful perfuming ingredient has to fulfil are known to a person skilled in the art and include, amongst others, a certain originality of the odoriferous note, stability and a certain price/performance ratio. Non-limiting examples for fragrant compounds which can be used with the α-keto esters of the invention will be mentioned below.

The α-keto esters of the above formula (I) release fragrant compounds upon exposure to light, in particular daylight. The α-keto esters of formula (I), however, are also capable of releasing a fragrant compound containing an olefin function from the group R'* in 1-position relative to the keto function, or a fragrant aldehyde or ketone which is derived from the alcohol R"*OH from which the organic part R"* is present in the ester function of the keto esters of the present invention, or even both.

From the above, it is clear that when reference is made to the organic part R"* of a fragrant alcohol R"*OH, R"* is the hydrocarbyl rest of said alcohol, e.g. a menthyl radical in case R"*OH is menthol.

The release of the fragrant compound from the keto esters occurs in an elimination reaction after an intramolecular transfer of an abstractable hydrogen radical, in γ-position to the α-keto function, to said keto function. The respective part of the molecule from which the hydrogen radical has been abstracted is subsequently released from the reduced keto ester, with concomitant formation of a double bond. The above is illustrated in the scheme below in which possible substituents in the respective parts of the molecules have been omitted for reasons of clarity. The double bonds which will be formed after elimination are indicated by dotted lines.

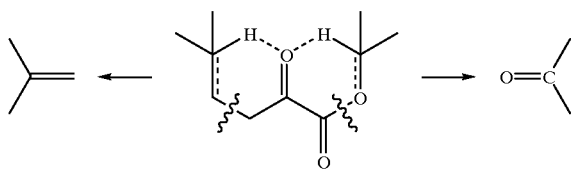

It is to be understood that the α-keto esters of the present invention can release only one or both molecules of fragrant compound per molecule of α-keto ester. When the hydrogen transfer to the α-keto function is able to occur from the one or the other side of said function, as illustrated above, a certain part of the molecules will release a ketone or aldehyde and a certain part will release the olefin compound. The proportions of the two products released depend on the relative rate of each hydrogen transfer reaction. According to the effect desired, the α-keto esters of the invention can be tailored to release exclusively a fragrant ketone or aldehyde, or exclusively a fragrant compound containing an olefin group, or both. When only one of the two classes of fragrant compounds is to be released from the α-keto esters of the invention, the part of the molecule from which no release shall occur does not contain an abstractable hydrogen atom in γ-position to the keto function, i.e. either no hydrogen atom at all is present in the said position, or it is one which is not abstracted.

It is also clear that the α-keto esters according to the invention can, in a first step, release the olefin compound under formation of a molecule which does not any longer contain an abstractable hydrogen atom in γ-position to the keto function (left side of the molecule as designed above); in a second step, this molecule can then release the ketone or aldehyde from the ester function.

A fragrance delivery system which contains the α-keto esters of the above formula (I) has the advantages that the release of the fragrant compound occurs in a more or less constant amount. No initial burst of very intensive odor which becomes imperceptible after a relatively short period of time occurs, as is often observed with volatile aldehydes or ketones or fragrant compounds containing an olefin group. With the α-keto esters of the present invention, such disadvantages are obviated because the esters will remain on a surface to which they have been applied or in the solution into which they have been incorporated. Upon exposure to light, the fragrant compound or compounds are released, and this reaction can provide perceptible amounts of the compound over days or weeks, depending, amongst others, on the amount or the concentration of the α-keto esters, the time of exposure to light and its intensity.

A further advantage of the a-keto esters according to formula (I) is the protection of the reactive, unstable aldehyde or keto function in the molecules to be released against degradation which may occur during storage.

Additionally, the α-keto esters of the present invention allow for the generation of mixtures of two different fragrant compounds, and in different proportions, if desired.

In principle, any fragrant aldehyde or ketone which is known in the art can be released from the α-keto esters of the invention in which they are chemically bound in the form of the ester of their corresponding secondary or primary alcohol.

Non-limiting examples for fragrant aldehydes which can be released from the α-keto esters include saturated and unsaturated linear and branched aldehydes from $C_6$ to $C_{13}$, citral, citronellal, campholenic aldehyde, cinnamic aldehyde, hexylcinnamic aldehyde, formyl pinane, hydroxycitronellal, cuminic aldehyde, vanillin, ethylvanillin, Lilial® [3-(4-tert-butylphenyl)-2-methylpropanal; origin: Givaudan-Roure SA, Vernier, Switzerland], Lyral® [4- and 3-(4-hydroxy-4-methylpentyl)-3-cyclohexene-1-carbaldehyde; origin: International Flavors and Fragrances, USA], Bourgeonal® [3-(4-tert-butylphenyl)propanal; origin: Quest International, Naarden, Netherlands], heliopropanal [3-(1,3-benzodioxol-5-yl)-2-methylpropanal; origin: Firmenich SA, Geneva, Switzerland], Zestover (2,4-dimethyl-3-cyclohexene-1-carbaldehyde; origin: Firmenich SA, Geneva, Switzerland), Trifernal® (3-phenylbutanal ; origin: Firmenich SA, Geneva, Switzerland), α-sinensal, (4-methylphenoxy) acetaldehyde, 1,3-benzodioxol-5-carboxaldehyde (heliotropine), Scentenal® [8(9)-methoxy-tricyclo[5.2.1.0. (2,6)]decane-3-(4)-carbaldehyde; origin: Firmenich SA, Geneva, Switzerland], Liminal® [(4R)-1-p-menthene-9-carbaldehyde; origin: Firmenich SA, Geneva, Switzerland], Cyclosal [3-(4-isopropylphenyl)-2-methylpropanal; origin: Firmenich SA, Geneva, Switzerland], ortho- and para-anisaldehyde, 3-methyl-5-phenylpentanal, Acropal® [4-(4-methyl-3-pentenyl)-3-cyclohexene-1-carbaldehyde; origin: Givaudan-Roure SA., Vernier, Switzerland], Intreleven® aldehyde (mixture of 10-undecenal and 9-undecenal; origin: International Flavors & Fragrances, USA), muguet aldehyde [(3,7-dimethyl-6-octenyl)acetaldehyde; origin: International Flavors & Fragrances, USA], 2,6-dimethyl-5-heptanal, Pre-cyclemone® B [1-methyl-4-(4-methyl-3-pentenyl)-3-cyclohexen-1-carbaldehyde; origin: International Flavors & Fragrances, USA] and Isocyclocitral® (2,4,6-trimethyl-3-cyclohexene-1-carbaldehyde; origin: International Flavors & Fragrances, USA).

Non-limiting examples for ketones which can be released from the α-keto esters include camphor, carvone, menthone, ionones, irones, damascenones and damacones, benzyl acetone (4-phenyl-2-butanone), 1-carvone, 4-(4-hydroxy-1-phenyl)-2-butanone (raspberry ketone), Hedione® (methyl dihydrojasmonate; origin: Firmenich SA, Geneva, Switzerland), Neobutenone [1-(5,5-dimethyl-1-cyclohexen-1-yl)-4-penten-1-one; origin: Firmenich SA, Geneva, Switzerland], Calone® (7-methyl-2H,4H-1,5-benzodioxepin-3-one; origin: C.A.L. SA, Grasse, France), Sulfox [(1R,4R)-8-mercapto-3-p-menthanone; origin: Firmenich SA, Geneva, Switzerland], Orivone® [4-(1,1-dimethylpropyl)-1-cyclohexanone; origin: International Flavors & Fragrances, USA], Delphone (2-pentyl-1-cyclopentanone; origin: Firmenich SA, Geneva, Switzerland), 2-naphthalenyl-1-ethanone, Veloutone (2,2,5-trimethyl-5-pentyl-1-cyclopentanone; origin: Firmenich SA, Geneva, Switzerland), 4-isopropyl-2-cyclohexen-1-one, Iso E Super® [isomer mixture of 1-(octahydro-2,3,8,8-tetrame-2-naphthalenyl)-1-ethanone; origin: International Flavors & Fragrances, USA], Plicatone [5-methyl-exo-tricyclo[6.2.1.0 (2,7)]undecan-4-one; origin: Firmenich SA, Geneva, Switzerland] ; and macrocyclic ketones such as, for example Exaltone® (cyclopentadecanone), Delta Muscenone (mixture of 3-methyl-4-cyclopentadecen-1-one and 3-methyl-5-cyclopentadecen-1-one) and Muscone (3-methyl-1-cyclopentadecanone), all from Firmenich SA, Geneva, Switzerland.

With respect to the fragrant compounds carrying an olefin group, in principle any compound containing such olefin group and, in addition, any osmophoric group known in perfumery can be used. As non-limiting examples for osmophoric groups, one can cite alcohol, ether, ester, aldehyde and keto groups, the thio analogues of the said groups, nitrile, nitro and olefin groups.

As non-limiting examples for fragrant compounds which carry an olefin group, there can be cited linalool, 1,3,5-undecatrienes, myrcene, myrcenol, dihydromyrcenol, nerolidol, sinensals, limonene, carvone, farnesenes, isopentyrate (1,3-dimethyl-3-butenyl isobutyrate; origin: Firmenich SA, Geneva, Switzerland), allyl 3-methylbutoxyacetate, eugenol, Rosalva (9-decen-1-ol; origin: International Flavors & Fragrances, USA), and allyl heptanoate.

It is quite obvious, however, that the invention is perfectly general and can relate to many other aldehydes, ketones and olefins which are useful as fragrant compounds. The person skilled in the art is quite able to choose these compounds from the general knowledge in the art and from the olfactive effect it is desired to achieve. The above list is therefore more illustrative for the compounds which are known to a person skilled in the art, and whose delivery can be improved. It is clearly quite impossible to cite in an exhaustive manner all aldehydes, ketones and olefins which have a pleasant odor and which can be used in the form of derivatives in the α-keto esters of formula (I) from which they are released upon exposure to light.

The α-keto esters of the present invention are in particular appropriate for delivering fragrant aldehydes, ketones and fragrant compounds containing an olefin group which are very volatile or which have a low perception threshold. Preferred aldehydes and ketones include citronellal, citral, hydroxycitronellal, Hedione®, Lilial®, raspberry ketone, anisaldehyde, menthone, Delphone, Orivone®, 2-naphthalenyl-1-ethanone, and aldehydes from $C_6$ to $C_{13}$, saturated or unsaturated linear or branched. Preferred fragrant compounds containing an olefin group include linalool, myrcene, myrcenol and Rosalva®.

In case the α-keto esters of the present invention are used to release exclusively aldehydes or ketones, the group R'* is hydrogen, phenyl, cyclohexyl or cyclopentyl, methyl, ethyl, n-propyl, isopropyl, sec-butyl, isobutyl or tert-butyl, i.e. groups which do not provide an abstractable hydrogen atom in γ-position to the α-keto function or which do not form a stable radical when a hydrogen radical is abstracted from them. In the latter case, small amounts of olefin may be formed which however do not interfere with the aldehyde or ketone released.

Likewise, when the α-keto esters of the present invention are used to release a fragrant compound containing an olefin group only, then the group R"* will be hydrogen or a methyl, ethyl or tert-butyl group, thus a group which does not provide an abstractable proton in γ-position to the α-keto function or which do not form a stable radical when a hydrogen radical is abstracted from them.

It is preferred when the fragrance delivery system of the present invention contains α-keto esters of formula (I) in which R"* is the organic part of a primary or secondary alcohol from which is derived a fragrant aldehyde or ketone and in which R'* is a phenyl, cyclohexyl or cyclopentyl group or a linear or branched alkyl group from $C_1$ to $C_4$, with the exception of an n-butyl group.

A fragrance delivery system containing the α-keto esters of formula (I) may comprise a solvent the choice of which is not supposed to be critical. Suitable classes of solvents include alcohols, ethers, esters, ketones, amines and aminoalcohols.

Depending on the general application conditions or on the product into which the α-keto esters according to the present invention are incorporated, one can sometimes also observe the release of alcohols R"*OH, due to saponification of the ester function, or due to reduction of the aldehyde or ketone formed by irradiation.

The α-keto esters of formula (I) can be prepared, on the one hand, by esteriication of the respective α-ketoacids with the primary or secondary alcohols which are the precursors of the fragrant aldehydes and ketones to be releasead. Another way for the preparation of the α-keto esters of the present invention is the reaction of the bis(oxalyl) ester of the primary or secondary precursor alcohol R"*OH with the Grignard compound of the appropriate group R'* as defined in formula (I). The reaction is illustrated in the scheme I below.

Scheme I

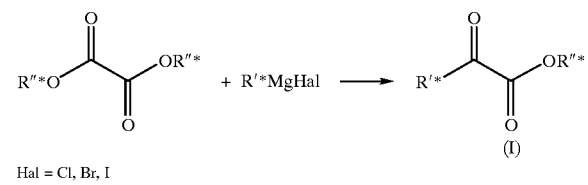

Hal = Cl, Br, I

The bis(oxalyl) ester is prepared from oxalyl chloride and the desired alcohol, see Synth. Commun. 1981, (11), 943–946 and Org. Synth. Coll. Vol. II 1943, 425–427.

Another synthetic route leading to the desired α-keto esters of formula (I) is the Grignard reaction of the readily available bis(oxalyl)esters of lower aliphatic alcohols such as, for example, methanol, ethanol or propanol, with the Grignard compound of the respective group R'*, resulting in the intermediate ester (II). This said ester (II) is then submitted to a transesterification reaction with the respective precursor alcohol R"*OH, to give the desired α-keto ester. This reaction is outlined in the following scheme II in which R'* and R"* have the meaning defined in formula (I). Hal is Cl, Br or I and R is a lower alkyl group such as, for example, methyl, ethyl, propyl or butyl.

Scheme II

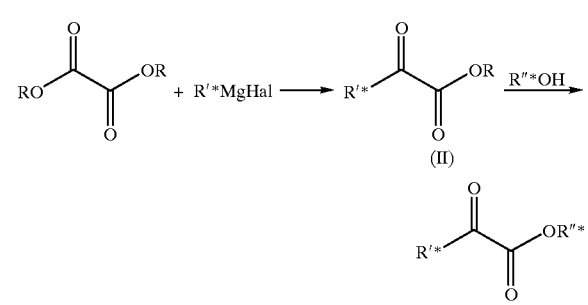

Various α-keto esters of formula (I) in which R'* is hydrogen or a phenyl or methyl group and R"* is derived from the alcohol precursor of a fragrant aldehyde are described in the literature.

Also known is hexyl (cyclohexyl)oxoacetate (see DE-OS 29 09 951 to Bayer AG, describing the use of the said compound as starting product for the synthesis of catalysts for the polymerisation of olefins), which would release n-hexanal upon irradiation.

In Biochem. Z. 1935, (277), p 426–436, there is described the synthesis of the (−)-bornyl ester of (4-methylphenyl) oxoacetic acid, i.e. (−) (1S,2R), 1,7,7-trimethylbicyclo [2.2.1]heptan-2-yl (4-methylphenyl)oxoacetate. The compound is characterized by its physical data.

There are furthermore known, from the chemical literature, various compounds according to the above formula (I) wherein OR"* is a menthyl or a benzyl group, with the groups R'* being various alkyl, alkenyl, cycloalkyl or phenyl groups as defined above.

There is nowhere found, however, any description or hint concerning the value of the compounds according to formula (I) in perfumery as a photosensitive molecule which will release a fragrant compound upon irradiation.

In the book of S. Arctander, Perfume and Flavors Chemicals, 1969, Montclair, N.J., USA, there are mentioned decyl 2-oxopropanoate, (Z)-3-hexenyl 2-oxopropanoate and 2-ethyl-3-methylbutyl 2-oxopropanoate, with a short description of their odor and their synthesis. It is not mentioned that the said molecules release fragrant compounds upon irradiation.

The release of the above-mentioned fragrant compounds from the delivery system occurs upon the exposure to light, e.g. the normal daylight which can penetrate through ordinary windows in houses and which is not particularly rich in UV-radiation. It goes without saying that upon exposure to bright sunlight, in particular outdoors, the release of the fragrant alcohol, aldehyde, ketone or alkene will occur faster and to a greater extent than upon exposure to the light in a room inside a building. Of course, the reaction which releases the fragrant compound from the delivery system can also be initiated by an appropriate artificial lamp.

The invention is also directed to a method of improving, enhancing or modifying odoriferous properties of a perfuming composition or a perfumed article comprising adding to the composition or article an effective amount of an α-keto ester as described above, provided that decyl 2-oxopropanoate, (Z)-3-hexynyl 2-oxopropanoate and 2-ethyl-3-methylbutyl 2-oxopropanoate are excluded.

The fragrance delivery systems of the present invention can be used in any application in which a prolonged, defined release of the above-mentioned fragrant compounds is desired. They therefore mostly find use in functional perfumery, in articles which are exposed to daylight when in use or which are applied to other articles which thereafter are exposed to daylight. Suitable examples include airfresheners in liquid and solid form which, with the delivery system of the present invention, still can release a fragrance when conventional air-fresheners, i.e. those not containing the system of the present invention, are exhausted. Other examples are various cleaners for the cleaning of surfaces of all kinds, e.g. window and household cleaners, all purposecleaners and furniture polish. The surfaces which have been cleaned with such cleaners will diffuse the smell of the perfume much longer than when cleaned with conventional cleaners. Other representative examples include detergents for fabric wash, fabric conditioners and fabric softeners which can also contain the delivery system of the present invention and which products can be in the form of powders, liquids or tablets. The fabrics and clothes washed or treated with such detergents or softeners will diffuse the fragrant compound even after having been stored for weeks or even months, in a dark place, like a wardrobe.

The release of the fragrant compound occurs in all the above-mentioned application examples. All possible types of window, household, all-purpose cleaners, air-fresheners, detergent, fabric wash and fabric softeners can be used with the fragrance delivery system of the present invention, which has revealed itself to be useful in all types of these above-mentioned application examples.

In the field of body care, the delivery systems according to the present invention have shown themselves to be particularly appropriate for an application in the hair care area, and specific examples include shampoos, hair conditioners, in particular leave-in conditioners, hairspray and other hair care products.

It can be said that generally all products which can be applied to a surface which is exposable to light may contain the system of the present invention. Examples include surfaces which belong to the human body, like skin or hair, surfaces in buildings and apartments, like floors, windows, tiles or furniture, or surfaces of fabrics, e.g. clothes. It is clear that the system of the invention can also be used to release fragrances from liquids, like in liquid air-fresheners. The possible applications of this type, however, appear to be less general than the application on the various surfaces mentioned wherein the ester of the invention will be deposed as a film on the respective surface.

Of course, the above examples are only illustrative and non-limiting as referring to preferred embodiments. All other current articles in functional and fine perfumery may contain the system of the present invention, and these articles include soaps, bath or shower gels, cosmetic preparations, body deodorants, and even perfumes or colognes.

In the above-cited applications, the device of the present invention can be used alone or with other perfuming ingredients, solvents and adjuvants of current use in the art. The nature and variety of these co-ingredients does not require a detailed description which, moreover could not be exhaustive, and a person skilled in the art will be able to choose said coingredients by his general knowledge and in function of the nature of the product to be perfumed and the olfactive effect sought. These perfuming ingredients belong to such varied chemical classes as alcohols, aldehydes, ketones, esters, ethers, acetates, nitrites, terpene hydrocarbons, nitrogen- or sulfur- containing heterocyclic compounds, as well as essential oils of natural or synthetic origin. By way of example, embodiments of compounds can be found in standard reference works, such as the book of S. Arctander, Perfume and Flavor Chemicals, 1969, Montclair, N.J., USA, or more recent versions thereof, or in other works of similar nature.

The proportions in which the system of the present invention can be incorporated in the various abovementioned products vary within a wide range of values. These values depend on the nature of the fragrant compound to be released, the nature of the article or product which is to be perfumed and the desired olfactive effect, as well as on the nature of the co-ingredients in a given composition when the system of the present invention is used in admixture with perfuming co-ingredients, solvents or adjuvants of current use in the art.

By way of example, one can cite typical concentrations of the order of 0.01 to 5%, or even 10% by weight relative to the weight of the consumer products cited above into which it is incorporated. Higher concentrations than those mentioned above can be used when the system is applied in perfuming compositions, perfumes or colognes.

The invention will now be described in greater detail in the following examples in which the temperatures are indicated in degrees centigrade and the abbreviations have the usual meaning in the art.

EMBODIMENTS OF THE INVENTION

General

The following chemicals were obtained from commercial sources: geraniol, magnesium turnings, 1,2-dichloroethane, 1,2-dibromoethane, 2-norbornyl bromide, bromocyclopentane, citronellol, decanol, 4-methoxybenzyl alcohol, Lilial®, (–)-menthol, 2-pentylcyclopentanol, 4-(1,1-dimethylpropyl)- 1-cyclohexanol, 1-(2-naphthalenyl) ethanol, oxalyl chloride, diethyl oxalate, 3-methyl-2-oxopentanoic acid, 2-oxopropionic acid, 2-oxobutanoic acid, bromocyclohexane, bromobenzene, 2-oxopentanoic acid, 4-bromo acetophenone, ethylene glycol, 2-bromotetradecane, 1-bromotetradecane.

Execution of photorelease assays and analysis for α-keto esters

Photorelease Assays

Photorelease assays were conducted on solutions or on films of the respective ester and will be described below in each of the examples referring to the respective mode of irradiation.

All samples were irradiated using a xenon lamp (Heraeus Suntest CPS at 460W/m2), a UV lamp (UVP Model UVL-28, 8W at 360 nm) or exposed to outdoor sunlight, as will be indicated for each sample in the respective examples.

Analysis

The mode of analysis for each sample which had been irradiated will be indicated in each respective example.

Analytical HPLC was carried out on a Spectra Physics instrument composed from a SP 8800 ternary pump, a SP 5750 injection valve, a SP 8780 autosampler, a Waters 490E UV detector and a Spectra Physics ChromJet integratorMacherey-Nagel Nucleosil 5 $C_{18}$ reversed phase column (125 ×4 mm i.d.) eluted with a gradient from acetonitrile/water 1:1 to pure acetonitrile during 20 min. The injection volume was 50 μl and the UV detector wavelength fixed at 220 nm.

Analytical GC for analysis of all-purpose/window cleaner applications: the on-column injections were carried out on a Carlo Erba MFC 500 using a precolumn (30 cm) and a Suppelco SPB-1 capillary column (30 m) at 115° C. for 8 min, then to 280° C., helium pressure 75 kPa, injection volume 2 μl. All other GC analyses were carried out on the same instrument equiped with a Fisons AS 800 autosampler using a J&W Scientific DB1 capillary column (15 m) at 70 or 80° C. for 10 min, then to 260° C., helium pressure 50 kPa, injection volume 0.5 μl.

Analytical GC for dynamic headspace analysis: Tenax cartridges were thermally desorbed in a PE ATD400 or a TDAS 5000 desorber. The volatiles were then analysed either with a Carlo Erba HRGC 5300 gas chromatograph coupled to Finnigan ITD-800 mass spectrometers using a Supelco SPB-1 capillary column (60 m, 0.75 mm i.d., film 1 micron) at 60° C. for 5 min then to 120° C. (3° C./min) and 280° C. (5° C./min) for the citronellal analysis, and at 100° C. then to 250° C. (5° C./min) for the menthone quantification or, alternatively, with a Carlo Erba Vega 6000 gas chromatograph using a Supelco SPB-1 capillary column (30 m, 0.53 mm i.d., film 1.5 micron) from 110° C. to 200° C. (6° C./min) using He as carrier gas in both cases.

EXAMPLE 1

Preparation of α-keto esters

The bis(3,7-dimethyl-6-octenyl)oxalate which was used for the synthesis of some of the α-keto esters described below was prepared as follows.

Oxalyl chloride (10 ml, 116 mmol) was added dropwise to a stirred solution of 36.37 g (233 mmol) of citronellol in 300 ml of pyridine at 0° C. over a period of 30 min. The formation of a white precipitate was observed. The solution was allowed to warm up at room temperature over night and was quenched with water, extracted with diethyl ether (2x), $H_2SO_4$ (10%) (2x), $NaHCO_3$ (10%) and saturated NaCl. The organic layer was dried over $Na_2SO_4$, concentrated at reduced pressure and filtered over a short plug ($SiO_2$, heptane/diethyl ether). Column chromatography ($SiO_2$, heptane/diethyl ether) gave 18.55 g (43%) of a colorless oil.

IR (neat): 2965s, 2925s, 2873m, 2856m, 1770s, 1745s, 1457m, 1380m, 1347w, 1312m, 1250w, 1170s, 1122w, 1044w, 941m, 886w, 831w, 792w, 756w, 742w.

$^1$H NMR (360 MHz, $CDCl_3$): 5.13-5.04 (m, I H); 4.40-4.23 (m, 2 H); 2.08-1.87 (m, 2 H); 1.85-1.71 (m, 1 H); 1.70-1.50 (m, 2 H); 1.68 (s, 3 H); 1.60 (s, 3 H); 1.43-1.29 (m, 1 H); 1.29-1.13 (m, 1 H); 0.94 (d,J=6.3, 3 H).

$^{13}$C NMR (90.6 MHz, $CDCl_3$): 158.04 (s); 131.45 (s); 124.42 (d); 65.59 (t); 36.91 (t); 35.08 (t); 29.42 (d); 25.70 (q); 25.36 (t); 19.36 (q); 17.65 (q).

MS (EI): 336 ($M^+$, 0.1); 228 (0.1); 183 (0.1); 165 (0.1); 138 (18); 123 (30); 109 (16); 95 (38); 81 (51); 69 (100); 55 (30); 41 (46); 29 (5).

a) 3,7-Dimethyl-6-octenyl-2-oxopropanoate (1)

A stirred solution of 5.56 g (63 mmol) of 2-oxo propionic acid and 19.68 g (126 mmol) of citronellol in 150 ml of toluene was heated for 35 h under reflux with azeotropic removal of water. After cooling to room temperature the reaction mixture was extracted with diethyl ether (2x), 10% $NaHCO_3$, sat. NaCl, dried ($Na_2SO_4$) and concentrated in vacuo. Column chromatography ($SiO_2$, pentane/ether 9:1) afforded 2.81 g (20%) of a colorless oil.

UV/Vis (hexane): 388 (sh, 3); 378 (sh, 5); 369 (sh, 8); 360 (sh, 10); 345 (14); 334 (14); 319 (sh, 12); 284 (sh, 9).

IR (neat): 2961m, 2915m, 2873m, 2856m, 1728s, 1454m, 1378m, 1357m, 1297m, 1266m, 1203w, 1134s, 1051m, 1024w, 982m, 937m, 830m, 771w, 720m, 663w.

$^1$H NMR (360 MHz, $CDCl_3$): 5.15-5.03 (m, 1 H); 4.37-4.18 (m, 2 H); 2.47 (s, 3 H); 2.10-1.88 (m, 2 H); 1.87-1.71 (m, 1 H); 1.71-1.47 (m, 2 H); 1.68 (s, 3 H); 1.60 (s, 3 H); 1.46-1.28 (m, 1 H); 1.28-1.12 (m, 1 H); 0.94 (d, J=6.3, 3 H).

$^{13}$C NMR (90.6 MHz, $CDCl_3$): 191.96 (s); 160.92 (s); 131.52 (s); 124.37 (d); 65.06 (t); 36.89 (t); 35.14 (t); 29.39 (d); 26.73 (q); 25.71 (q); 25.33 (t); 19.36 (q); 17.66 (q).

MS (EI): 226 ($M^+$, 3); 209 (1); 208 (5); 198 (1), 184 81); 183 (9); 165 (2); 156 (1);
155 (14); 139 (1); 138 (15); 137 (20); 136 (1); 124 (3); 123 (29); 121 (3); 111 (1); 110 (5); 109 (20); 99 (1); 97 (2); 96 (8); 95 (45); 94 (2); 93 (1); 91 (1); 90 (1); 84 (1); 83 (15); 82 (28); 81 (51); 80 (2); 79 (2); 77 (1); 71 (1); 70 (10); 69 (100); 68 (14); 67 (23); 66 (1); 65 (2); 57 (5); 56 (8); 55 (34); 54 (2); 53 (7); 44 (1); 43 (41); 42 (5); 41 (40); 40 (2); 39 (6); 29 (4); 27 (3).

b) 3,7-Dimethyl-6-octenyl-2-oxobutanoate (2)

The synthesis was carried out as described above under a) with 6.43 g (63 mmol) of 2-oxo butyric acid, 19.68 g (126 mmol) of citronellol and 150 ml of toluene (24 h). Column chromatography ($SiO_2$, pentane/ether 9:1) afforded 7.80 g (52%) of a colorless oil.

UV/Vis (hexane): 397 (sh, 1); 383 (sh, 3); 373 (sh, 6); 356 (sh, 12); 341 (16); 330 (16); 318 (sh, 14); 268 (sh, 12).

IR (neat): 2961m, 2914m, 2879m, 2857m, 1725s, 1456m, 1404w, 1379m, 1351w, 1273m, 1242m, 1173w, 1144m, 1097s, 1041m, 982m, 946w, 881w, 830m, 760w, 737w, 700m, 678m.

$^1$H NMR (360 MHz, $CDCl_3$): 5.14-5.02 (m, 1 H); 4.40-4.20 (m, 2 H); 2.86 (q, J=7.3, 2 H); 2.09-1.88 (m, 2 H); 1.87-1.68 (m, 1 H); 1.68 (s, 3 H); 1.68-1.45 (m, 2 H); 1.60 (s, 3 H); 1.45-1.29 (m, 1 H); 1.29-1.15 (m, 1 H); 1.13 (t, J=7.1, 3 H 0.94 (d, J=6.3, 3 H).

¹³C NMR (90.6 MHz, CDCl₃): 195.09 (s); 161.32 (s); 131.51 (s); 124.40 (d); 64.87 (t); 36.90 (t); 35.17 (t); 32.89 (t); 29.40 (d); 25.71 (q); 25.34 (t); 19.37 (q); 17.66 (q); 6.97 (q).

MS (EI): 240 (M⁺, 1); 222 (3); 212 (2); 184 (1); 183 (8); 165 (1); 156 (1); 155 (12); 139 (3); 138 (20); 137 (15); 136 (1); 124 (3); 123 (31); 121 (3); 111 (2); 110 (4); 109 (16); 104 (2); 99 (1); 97 (3); 96 (9); 95 (43); 94 (3); 93 (2); 91 (1); 85 (1); 84 (2); 83 (17); 82 (31); 81 (51); 80 (3); 79 (2); 77 (1), 71 (1); 70 (8); 69 (100); 68 (13); 67 (19); 66 (1); 65 (2); 58 (2); 57 (63); 56 (7); 55 (30); 54 (2); 53 (6); 43 (6); 42 (4); 41 (38); 40 (1); 39 (5); 29 (17); 28 (2); 27 (5).

c) 3,7-Dimethyl-6-octenyl 3-methyl-2-oxopentanoate (3)

The synthesis was carried out as described above under a), using 4.85 g (38 mmol) of 3-methyl-2-oxo pentanoic acid and 11.66 g (74 mmol) of citronellol in 130 ml of toluene, for 72 h. Column chromatography (SiO₂, toluene/EtOAc) afforded 10 g of crude product, which was fractionally distilled to give 3.65 g (36%) of a colorless oil. B.p. 94° C./2x10¹ Pa.

UV/Vis (hexane): 394 (sh, 4), 382 (sh, 10), 374 (sh, 10), 365 (sh, 10), 350 (sh, 20), 336 (20), 268 (sh, 30), 241 (sh, 180).

IR (neat): 2966s, 2929s, 2877m, 1749m, 1728s, 1460m, 1380m, 1267m, 1254m, 1165m, 1115w, 1087w, 1051m, 1001w, 961w, 829w.

¹H NMR (360 MHz, CDCl₃): 5.12-5.04 (m, 1 H); 4.36-4.24 (m, 2 H); 3.18-3.06 (m, 1 H); 2.08-1.88 (m, 2 H); 1.86-1.67 (m, 2 H); 1.68 (s, 3 H); 1.65-1.10 (m, 5 H); 1.60 (s, 3 H); 1.28 (d, J=6.8, 3 H); 0.94 (d, J 6.4, 3 H); 0.92 (t, J=7.6, 3 H).

¹³C NMR (90.6 MHz, CDCl₃): 198.22 (s); 162.21 (s); 131.51 (s); 124.40 (d); 64.74 (t); 43.64 (d); 36.92 (t); 35.23 (t); 29.43 (d); 25.71 (q); 25.36 (t); 24.93 (t); 19.35 (q); 17.66 (q); 14.55 (q); 11.35 (q).

MS (EI): 268 (M⁺, 1); 250 (1); 240 (1); 207 (1); 183 (2); 155 (2); 138 (10); 123 (14); 109 (7); 95 (18); 85 (32); 81 (26); 69 (51); 57 (100); 41 (53); 29 (18).

d) 3,7-Dimethyl-6-octenyl 2-oxopentanoate (4)

The synthesis was carried out as described above under a), using 4.33 g (37 mmol) of 2-oxo pentanoic acid and 11.65 g (75 mmol) of citronellol. Column chromatography (SiO₂, toluene/EtOAc and SiO₂, heptane/diethyl ether) afforded 3.79 g of crude product, which was distilled (Kugelrohr) to give 2.52 g (27%) of a colorless oil.

UV/Vis (hexane): 398 (sh, 1), 376 (sh, 10), 357 (sh, 10), 342 (sh, 20), 331 (20), 281 (sh, 20), 268 (sh, 30), 241 (sh, 280).

IR (neat): 2965s, 2931s, 2877m, 1750m, 1728m, 1457m, 1380m, 1287w, 1261m, 1178w, 1146w, 1118m, 1055m, 1037w, 943w, 832w.

¹H NMR (360 MHz, CDCl₃): 5.13-5.03 (m, 1 H); 4.36-4.21 (m, 2 H); 2.80 (t, J=7.31, 2 H); 2.10-1.89 (m, 2 H); 1.83-1.70 (m, 1 H); 1.68 (s, 3 H); 1.67 (q, J=7.3, 2 H); 1.63-1.47 (m, 2 H); 1.60 (s, 3 H); 1.45-1.29 (m, 1 H); 1.28-1.12 (m, 1 H); 0.96 (t, J=6.9, 3 H); 0.94 (d, J=6.3, 3 H).

¹³C NMR (90.6 MHz, CDCl₃): 194.63 (s); 161.44 (s); 131.52 (s); 124.40 (d); 64.88 (t); 41.21 (t); 36.91 (t); 35.19 (t); 29.43 (d); 25.71 (q); 25.35 (t); 19.37 (q); 17.67 (q); 16.54 (t); 13.52 (q).

MS (EI): 254 (M⁺, 1); 236 (2); 226 (1); 193 (1); 183 (6); 165 (1); 155 (7); 138 (15); 137 (10); 123 (26); 118 (3); 109 (17); 95 (41); 83 (15); 82 (32); 81 (54); 71 (87); 69 (100); 67 (23); 55 (34); 43 (66); 41 (72); 27 (14).

e) 3,7-Dimethyl-6-octenyl oxo(phenyl)acetate (5)

A Grignard reagent prepared from 3.14 g of 1-bromobenzene (20 mmol) and 0.55 g of magnesium (22 mmol) in THF was added dropwise to a stirred solution of 8.0 g (22 mmol) of bis(3,7-dimethyl-6-octenyl)oxalate in 50 ml of THF at −78° C. The mixture was slowly warmed to −10° C., quenched with 25–30 ml of a saturated solution of NH₄Cl and left stirring for 30 min. The reaction mixture was extracted with diethyl ether and water (3x) and the organic phase dried over Na₂SO₄. MPLC on a Lobar column (SiO₂ Merck, heptane/diethyl ether) afforded 3.5 g (61%) of the pure product as a bright yellow oil.

UV/Vis (hexane): 370 (sh, 30), 352 (40), 340 (sh, 40), 294 (sh, 1020), 252 (10350), 248 (10360).

IR (neat): 3065w, 2962s, 2926s, 2872m, 2855m, 1738s, 1693s, 1597m, 1581m, 1451m, 1379m, 1322m, 1313m, 1300m, 1246w, 1198s, 1175s, 1122w, 1042w, 1030w, 1003m, 998m, 941w, 831w.

¹H NMR (360 MHz, CDCl₃): 8.04-7.97 (m, 2 H); 7.69.7.62 (m, 1 H); 7.55-7.45 (m, 2 H); 5.12-5.03 (m, 1 H); 4.50-4.36 (m, 2 H); 2.15-1.90 (m, 2 H); 1.90-1.75 (m, 1 H); 1.75-1.50 (m, 2 H); 1.66 (s, 3 H); 1.59 (s, 3 H); 1.45-1.32 (m, 1 H); 1.32-1.15 (m, 1 H); 0.96 (d, J=6.3, 3 H).

¹³C NMR (90.6 MHz, CDCl₃): 186.50 (s); 164.02 (s); 134.87 (d); 132.56 (s); 131.51 (s); 130.02 (d); 128.90 (d); 124.40 (d); 64.85 (t); 36.93 (t); 35.30 (t); 29.44 (d); 25.69 (q); 25.38 (t); 19.38 (q); 17.66 (q).

MS (EI): 288 (M⁺, 1); 270 (4); 260 (1); 227 (1); 215 (1); 187 (1); 183 (1); 174 (1); 165 (1); 155 (4); 152 (3); 138 (9); 137 (10); 134 (2); 123 (11); 109 (8); 106 (10); 105 (100); 96 (3); 95 (20); 83 (3); 82 (12); 81 (24); 80 (2); 78 (3); 77 (36); 70 (3); 69 (26); 68 (5); 67 (10); 57 (3); 56 (3); 55 (11); 53 (3); 51 (10); 43 (4); 42 (3); 41 (28); 39 (5); 29 (4); 27 (4).

f) 3,7-Dimethyl-6-octenyl (4-acetylphenyl)oxoacetate (6)

In the first step, 2-(4-bromomethyl)-2-methyl-1,3-dioxolane was prepared as follows. 10.0 g (50 mmol) of 4-bromo acetophenone, 7.0 g (112 mmol) of ethylene glycol and a few crystals of p-toluene sulphonic acid were dissolved in 100 ml of toluene and heated overnight under reflux with azeotropic removal of water. After cooling to room temperature the reaction mixture was concentrated in vacuo. Column chromatography (SiO₂, heptane/diethyl ether) afforded 11.4 g (93%) of a colorless oil which easily crystallized.

UV/Vis (hexane): 287 (sh, 400), 274 (sh, 1300), 270 (sh, 1800), 259 (sh, 6700), 252 (7800), 227 (sh, 61800), 220 (75600), 217 (sh, 75000).

IR (neat): 3084w, 3060w, 2990m, 2957s, 2928s, 2890s, 2856m, 2670w, 1911w, 1691m, 1657w, 1591m, 1575w, 1482m, 1470w, 1443m, 1393m, 1373m, 1249m, 1222w, 1196s, 1144m, 1118m, 1092m, 1079m, 1040s, 1010s, 947m, 873s, 826s.

¹H NMR (360 MHz, CDCl₃): 7.49-7.42 (m, 2 H); 7.39-7.32 (m, 2 H); 4.08-3.96 (m, 2 H); 3.80-3.69 (m, 2 H); 1.62 (s, 3 H).

¹³C NMR (90.6 MHz, CDCl₃): 142.49 (s); 131.30 (d); 127.17 (d); 121.86 (s); 108.43 (s); 64.47 (t); 27.52 (q).

MS (EI): 244, 242 (M⁺, 1, 1); 230 (14); 229 (97); 227 (100); 213 (5); 211 (5); 186 (4); 185, 183 (51, 53); 171 (2); 169 (2); 157, 155 (14, 14); 148 (4); 133 (5); 105 (2); 104 (8); 103 (9); 102 (8); 101 (2); 89 (3); 87 (26); 78 (2); 77 (12); 76 (16); 75 (14); 74 (7); 73 (2); 63 (4); 62 (2); 51 (7); 50 (13); 43 (41); 39 (3); 29 (7).

The thus obtained compound was then used as starting product for the synthesis of 3,7-dimethyl-6-octenyl [4-(2-methyl-1,3-dioxolan-2-yl)phenyl]oxoacetate. The synthesis was carried out as described above under e), using 4.66 g (20 mmol) of the above-prepared dioxolane, 0.54 g (22 mmol) of magnesium and 8.0 g (22 mmol) of bis(3,7-dimethyl-6-octenyl)oxalate. Column chromatography (SiO₂, heptane/ diethyl ether) afforded 4.35 g (58%) of the product as a slightly yellow oil.

UV/Vis (hexane): 370 (sh, 40), 353 (60), 340 (sh, 60), 296 (sh, 1300), 258 (13890).

IR (neat): 2963s, 2926s, 1736s, 1690s, 1607s, 1573m, 1505w, 1455m, 1407m, 1374m, 1347w, 1314m, 1294w, 1250m, 1199s, 1175s, 1146w, 1122w, 1100w, 1078m, 1039m, 1018w, 989m, 948w, 890w, 876m, 861m, 833w.

$^1$H NMR (360 MHz, CDCl$_3$): 7.98 (d, J=8.3, 2 H); 7.62 (d, J=8.7, 2 H); 5.12-5.04 (m, 1 H); 4.50-4.36 (m, 2 H); 4.13-4.00 (m, 2 H); 3.82-3.70 (m, 2 H); 2.10-1.90 (m, 2 H); 1.90-1.75 (m, 1 H); 1.72-1.54 (m, 2 H); 1.67 (s, 3 H); 1.65 (s, 3 H); 1.60 (s, 3 H); 1.45-1.32 (m, 1 H); 1.30-1.16 (m, 1 H); 0.96 (d, J=6.3, 3 H).

$^{13}$C NMR (90.6 MHz, CDCl$_3$): 186.04 (s); 163.97 (s); 150.64 (s), 132.12 (s); 131.53 (s); 130.15 (d); 125.97 (d); 124.39 (d); 108.39 (s); 64.89 (t); 64.65 (2x) (t); 36.93 (t); 35.30 (t); 29.44 (d); 27.38 (q); 25.70 (q); 25.37 (t); 19.38 (q); 17.66 (q).

MS (EI): 374 (M$^+$, 7); 359 (8); 356 (3); 289 (1); 220 (2); 205 (1); 192 (32); 191 (100); 176 (2); 160 (2); 155 (2); 148 (24); 138 (16); 133 (6); 123 (14); 119 (76); 109 (9); 104 (15); 95 (22); 91 (8); 87 (18); 81 (30); 69 (26); 55 (10); 43 (12); 41 (21); 29 (3).

3,7-Dimethyl-6-octenyl (4-acetylphenyl)oxoacetate (6)

5 ml of H$_2$SO$_4$ (50%) were added to a solution of 4.2 g (13 mmol) of the product obtained in the above step in 30 ml of THF. The reaction mixture was heated at 40° C. for 5 h, then extracted with diethyl ether (2x), and saturated solutions of NaHCO$_3$ (2x) and NaCl (2x). The organic layer was dried over Na$_2$SO$_4$ and concentrated. Column chromatography (SiO$_2$, heptane/diethyl ether) yielded 2.0 g (47%) of a yellow oil.

UV/Vis (hexane): 384 (sh, 60), 367 (sh, 100), 343 (sh, 150), 310 (sh, 1230), 301 (sh, 1660), 266 (17910), 260 (18440).

IR (neat): 3051w, 2964s, 2926s, 2872m, 2856m, 1736s, 1693s, 1607w, 1570m, 1500m, 1457m, 1434m, 1407m, 1379m, 1359m, 1318m, 1307m, 1260s, 1199s, 1176s, 1117w, 1075m, 992s, 959m, 861m, 832m.

$^1$H NMR (360 MHz, CDCl$_3$): 8.17-8.02 (m, 4 H); 5.12-5.04 (m, 1 H); 4.53-4.37 (m, 2 H); 2.66 (s, 3 H); 2.14-1.90 (m, 2 H); 1.90-1.75 (m, 1 H); 1.73-1.53 (m, 2 H); 1.67 (s, 3 H); 1.60 (s, 3 H); 1.46-1.32 (m, 1 H); 1.32-1.12 (m, 1 H); 0.96 (d, J=6.3, 3 H).

$^{13}$C NMR (90.6 MHz, CDCl$_3$): 197.19 (s); 185.55 (s); 163.25 (s); 141.33 (s); 135.67 (s); 131.57 (s); 130.28 (d); 128.56 (d); 124.34 (d); 65.19 (t); 36.91 (t); 35.26 (t); 29.43 (d); 26.94 (q); 25.70 (q); 25.35 (t); 19.37 (q); 17.67 (q).

MS (EI): 330 (M$^+$, 4); 312 (1); 302 (1); 281 (1); 269 (1); 194 (4); 193 (2); 183 (1); 176 (2); 165 (1); 161 (1); 155 (2); 149 (5); 148 (43); 147 (100); 138 (4); 137 (11); 133 (1); 132 (2); 123 (10); 120 (4); 119 (11); 110 (2); 109 (10);105 (2); 104 (12); 96 (4); 95 (21); 91 (15); 83 (5); 82 (13); 81 (29); 77 (6); 76 (8); 69 ; (38); 698 (5); 67 (11); 65 (3); 57 (3); 56 (3); 55 (12); 53 (3); 50 (3); 43 (15); 41 (30); 39 (5); 29 (4); 27 (3).

g) 3,7-Dimethyl-6-octenyl 3-methyl-2-oxopentadecanoate (7)

The compound was prepared as described above under e), using 5.0 g (18 mmol) of 2-bromotetradecane, 0.58 g (24 mmol) of magnesium and 7.32 g (20 mmol) of bis(3,7-dimethyl-6-octenyl)oxalate. Column chromatography (SiO$_2$, heptane/ diethyl ether) afforded 2.52 g (34%) of a colorless oil.

UV/Vis (hexane): 394 (sh, 4), 383 (sh, 10), 373 (sh, 10), 365 (sh, 20), 349 (sh, 20), 336 (20), 284 (sh, 10), 269 (sh, 20), 241 (sh, 140).

IR (neat): 3440w, 2958s, 2924s, 2854s, 2730w, 1749s, 1725s, 1460m, 1378m, 1350w, 1266m, 1173w, 1146w, 1112w, 1053m, 1032m, 943w, 887w, 830w.

$^1$H NMR (360 MHz, CDCl$_3$): 5.13-5.04 (m, 1 H); 4.36-4.23 (m, 2 H); 3.23-3.10 (m, $^1$H); 2.10-1.87 (m, 2 H); 1.87-1.64 (m, 1 H); 1.68 (s, 3 H); 1.64-1.47 (m, 2 H); 1.60 (s, 3 H); 1.46-1.16 (m, 24 H); 1.13 (d, J=6.7, 3 H); 0.94 (d, J=6.3, 3 H); 0.88 (t, J=6.9, 3 H).

$^{13}$C NMR (90.6 MHz, CDCl$_3$): 198.33 (s); 162.20 (s); 131.50 (s); 124.40 (d); 64.75 (t); 42.21 (d); 36.93 (t); 35.23 (t); 31.92 (t); 29.68 (t); 29.66 (2x) (t); 29.59 (2x) (t); 29.45 (2x) (t); 29.37 (t); 27.01 (t); 25.71 (q); 25.37 (t); 22.70 (t); 19.35 (q); 17.66 (q); 15.01 (q); 14.12 (q).

MS (EI): 408 (M$^+$, 1); 390 (1); 380 (1); 347 (1); 294 (1); 272 (1); 255 (4); 205 (1); 197 (3); 184 (2); 183 (12); 165 (1); 155 (8); 141 (4); 139 (9); 138 (76); 137 (21); 127 (7); 123 (46); 113 (9); 109 (19); 99 (15); 96 (15); 95 (57); 94 (8); 85 (47); 83 (25); 82 (52); 81 (89); 80 (14); 71 (65); 70 (10); 69 (100); 68 (10); 67 (18); 57 (94); 56 (17); 55 (51); 43 (61); 41 (69); 39 (7); 29 (15); 27 (6).

h) 3,7-Dimethyl-6-octenyl 2-oxohexadecanoate (8)

The compound was prepared as described above under e), using 5.54 g (20 mmol) of 1-bromotetradecane, 0.54 g (22.5 mmol) of magnesium and 8.0 g (22 mmol) of bis(3,7-dimethyl-6-octenyl)oxalate. Column chromatography (SiO$_2$, heptane/diethyl ether) afforded 3.21 g (39%) of a colorless oil.

UV/Vis (hexane): 376 (sh, 10), 359 (sh, 20), 343 (sh, 20), 279 (260), 272 (sh, 250), 242 (530).

IR (neat): 2958m, 2924s, 2854s, 1728s, 1465m, 1458m, 1400w, 1378m, 1271m, 1128w, 1088w, 1062m, 945w, 831w.

$^1$H NMR (360 MHz, CDCl$_3$): 5.12-5.03 (m, 1 H); 4.35-4.21 (m, 2 H); 2.81 (t, J=7.3, 2 H); 2.09-1.88 (m, 2 H); 1.87-1.69 (m, 1 H); 1.68 (s, 3 H); 1.69-1.47 (m, 2 H); 1.60 (s, 3 H); 1.45-1.14 (m, 26 H); 0.94 (d, J=6.3, 3 H); 0.88 (t, J=6.9, 3 H).

$^{13}$C NMR (90.6 MHz, CDCl$_3$): 194.77 (s); 161.48 (s); 131.49 (s); 124.41 (d); 64.86 (t); 39.38 (t); 36.93 (t); 35.20 (t); 31.96 (t); 29.68 (3x) (t); 29.61 (t); 29.45 (2x) (t); 29.39 (t); 29.33 (t); 29.01 (t); 25.71 (q); 25.37 (t); 23.05 (t); 22.71 (t); 19.38 (q); 17.66 (q); 14.12 (q).

MS (EI): 390 (1), 225 (1), 183 (14), 165 (1), 155 (8), 139 (7), 138 (55); 137 (28); 124 (6), 123 (52), 121 (5), 111 (4), 110 (7), 109 (27), 97 (9), 96 (16), 95 (70), 94 (8), 85 (16), 83 (28), 82 (50), 81 (97), 80 (10), 71 (26), 70 (11), 69 (100), 68 (11), 67 (21), 57 (54), 56 (12), 55 (47), 43 (48), 42 (10), 41 (55), 39 (7), 29 (12).

i) 3,7-Dimethyl-6-octenyl (cyclohexyl)oxoacetate (9)

The compound was prepared as described above under e), using 3.24 g (20 mmol) of freshly distilled 1-bromocyclohexane, 0.55 g (22 mmol) of magnesium and 8.0 g (22 mmol) of bis(3,7-dimethyl-6-octenyl)oxalate. MPLC on a Lobar column (SiO$_2$ Merck, heptane/diethyl ether) finally afforded 1.69 g (29%) of the pure product as a colorless oil.

UV/Vis (hexane): 394 (sh, 4), 375 (sh, 11), 366 (sh, 14), 350 (sh, 18), 338 (19).

IR (neat): 2932s, 2856m, 1747m, 1727s, 1451m, 1379m, 1311w, 1276m, 1230m, 1183w, 1173w, 1140m, 1118w, 1082m, 1067m, 1050w, 1029w, 997m, 942w, 895w, 837w.

$^1$H NMR (360 MHz, CDCl$_3$): 5.12-5.04 (m, 1 H); 4.36-4.22 (m, 2 H); 3.07-2.95 (m, 1H); 2.09-1.85 (m, 4 H); 1.85-1.64 (m, 3 H); 1.68 (s, 3 H); 1.64-1.47 (m, 2 H); 1.60 (s, 3 H); 1.43-1.13 (m, 8 H); 0.93 (d, J=6.3, 3 H).

$^{13}$C NMR (90.6 MHz, CDCl$_3$): 197.65 (s); 162.17 (s); 131.51 (s); 124.39 (d); 64.71 (t); 46.34 (d); 36.91 (t); 35.21 (t); 29.44(d); 27.46 (t); 25.72 (t); 25.36 (t); 25.30 (t); 19.35 (q); 17.66 (q).

MS (EI): 294 (M⁺, 1); 276 (1); 266 (1); 233 (1); 193 (1); 183 (4); 165 (1); 155 (2); 139 (2); 138 (13); 137 (4); 123 (14); 112 (2); 111 (16); 110 (3); 109 (6); 96 (4); 95 (16); 94 (2); 84 (7); 83 (100); 82 (15); 81 (22); 80 (3); 70 (2); 69 (29); 68 (4); 67 (11); 56 (4); 55 (42); 54 (3); 53 (5); 43 (4); 42 (4); 41 (38); 39 (8); 29 (6); 27 (4), k) (E)-3,7-Dimethyl-2,6-octadienyl (cyclohexyl)oxoacetate (10)

In the first step, ethyl (cyclohexyl)oxoacetate was prepared as follows. A Grignard reagent prepared from 24.45 g of 1-bromocyclohexane (0.18 mol) and 4.32 g of magnesium (0.15 mol) in 70 ml THF was added dropwise (during a period of 40 min) to a stirred solution of 14.6 g (0.10 mol) of diethyl oxalate in 150 ml of THF at −70° C. The formation of a precipitate was observed and another 100 ml of THF were added. The mixture was slowly warmed to −10° C. and poured onto ice, saturated with NaCl, extracted with diethyl ether (2x) and washed with a sat. solution of $NH_4Cl$ (2x) and water (pH~7). The organic phase was dried over $Na_2SO_4$ and concentrated. Fractional distillation gave 9.86 g (54%) of a colorless oil.

B.p. 54° C./0.1-1.5 mbar. UV/Vis (hexane): 394 (sh, 5); 375 (sh, 10); 366 (sh, 15); 350 (sh, 20); 337 (20); 285 (sh, 7).

IR (neat): 2982w, 2930m, 2854m, 1722s, 1449m, 1366w, 1272m, 1229m, 1184w, 1140m, 1112w, 1081m, 1066s, 1014m, 991m, 923w, 894w, 855w.

¹H NMR (360 MHz, $CDCl_3$): 4.32 (q, J=7.1, 2 H); 3.1-2.97 (m, 1 H); 1.97-1.85 (m, 2 H); 1.85-1.74 (m, 2 H); 1.74-1.64 (m, 1 H); 1.45-1.13 (m, 5 H); 1.37 (t, J=71, 3 H).

¹³C NMR (90.6 MHz, $CDCl_3$): 197.65 (s); 162.03 (s); 62.19 (t); 46.29 (d); 27.51 (t); 25.73 (t); 25.32 (t); 14.06 (q).

MS (EI): 184 (M⁺, 2); 112 (3); 111 (33); 110 (3); 84 (6); 83 (100); 81 (3); 79 (2); 77 (1); 68 (1); 67 (5); 65 (1); 56 (3); 55 (54); 54 (5); 53 (5); 51 (1); 43 (2); 42 (3); 41 (23); 40 (2); 39 (12); 30 (1); 29 (20); 28 (3); 27 (13); 26 (1).

(E)-3,7-Dimethyl-2,6-octadienyl (cyclohexyl)oxoacetate (10)

A solution of 25.20 g (137 mmol) of the product obtained above, 25.56 g (166 mmol) of geraniol and 1 ml of $NaOCH_3$ (30% in methanol) in 150 ml of cyclohexane was heated under reflux overnight. After cooling to room temperature the reaction mixture was taken up in ether, washed with a sat. solution of NaCl (pH≠7), dried ($Na_2SO_4$), filtered and concentrated. Column chromatography ($SiO_2$, heptane/ether 9:1) and fractional distillation afforded 23.36 g (58%) of a colorless oil.

B.p. 130° C./0.1 mbar.

UV/Vis (hexane): 394 (sh, 5); 384 (sh, 8); 375 (sh, 14); 366 (sh, 17); 358 (sh, 20); 350 (sh, 22); 336 (24).

IR (neat): 2926m, 2853m, 1743m, 1721s, 1670w, 1449m, 1376m, 1341w, 1331w, 1309w, 1273m, 1267m, 1227m, 1183w, 1139m, 1111w, 1080m, 1063s, 1027w, 993s, 915m, 895w, 830w, 805w, 787w, 739w, 729w, 718w.

¹H NMR (360 MHz, $CDCl_3$): 5.45-5.35 (m, 1 H); 5.12-5.03 (m, 1 H); 4.76 (d, J=7.1, 2 H); 3.09-2.95 (m, 1 H); 2.17-1.98 (m, 4 H); 1.98-1.85 (m, 2 H); 1.84-1.75 (m, 2 H); 1.74 (s, 3 H); 1.73-1.62 (m, 1 H); 1.68 (s, 3 H); 1.60 (s, 3 H); 1.43-1.14 (m, 5 H).

¹³C NMR (90.6 MHz, $CDCl_3$): 197.70 (s); 162.08 (s); 143.97 (s); 131.97 (s); 123.59 (d); 117.16 (d); 62.90 (t); 46.38 (d); 39.55 (t); 27.49 (t); 26.23 (t); 25.73 (t); 25.67(q); 25.31 (t); 17.69(q); 16.58(q).

MS (EI): 292 (M⁺, 1); 205 (1); 179 (1); 138 (3); 137 (24); 136 (4); 135 (3); 123 (1); 122 (1); 121 (2); 112 (1); 111 (9); 107 (2); 105 (1); 96 (1); 95 (9); 94 (1); 93 (9); 92 (2); 91 (3); 84 (4); 83 (54); 82 (4); 81 (55); 80 (2); 79 (4); 77 (3); 70 (6); 69 (100); 68 (12); 67 (12); 65 (1); 56 (1); 55 (24); 54(2); 53 (6); 43 (2); 42 (2); 41 (25); 40 (1); 39 (5); 29 (2); 27 (2).

l) Decyl (cyclohexyl)oxoacetate (11)

The synthesis was carried out as described above under k), using 6.21 g (33.4 mmol) of ethyl (cyclohexyl) oxoacetate, 5.75 g (36.4 mmol) of decanol, 0.5 ml of $NaOCH_3$ (30% in methanol) and 50 ml of cyclohexane. Fractional distillation afforded 3.85 g (39%) of a colorless oil.

B.p. 118-126° C./0.2 mbar.

UV/Vis (hexane): 394 (sh, 4); 382 (sh, 8); 376 (sh, 11); 367 (sh, 14); 358 (sh, 17); 350 (sh, 19); 336 (19); 314 (sh, 17); 302 (sh, 15).

IR (neat): 2924s, 2852m, 1745m, 1723s, 1466m, 1450m, 1377w, 1330w, 1310w, 1290w, 1274m, 1229m, 1183w, 1139m, 1117w, 1082m, 1065m, 1028w, 995m, 929w, 895w, 867w, 802w, 785w, 720m, 662w.

¹H NMR (360 MHz, CDCl3): 4.24 (t, J=6.7, 2 H); 3.07-2.96 (m, 1 H); 1.98-1.85 (m, 2 H); 1.85-1.60 (m, 5 H); 1.44-1.14 (m, 19 H); 0.88 (t, J=6.9, 3 H).

¹³C NMR (90.6 MHz, $CDCl_3$): 197.70 (s); 162.22 (s); 66.27 (t); 46.37 (d); 31.90 (t); 29.51 (t); 29.49 (t); 29.30 (t); 29.17 (t); 28.42 (t); 27.48 (t); 25.80 (t); 25.74 (t); 25.32 (t); 22.69 (t); 14.11 (q).

MS (EI): 296 (M⁺, 2); 185 (1); 158 (1); 156 (1); 112 (7); 111 (88); 110 (3); 85 (2); 84 (7); 83 (100); 81 (1); 79 (1); 71 82); 70 (1); 69 (2); 68 (1); 67 (3); 57 (5); 56 (3); 55 (23); 54 (1); 53 (1); 43 (7); 42 (2); 41 (10); 39 (2); 29 (2); 27 (1).

m) 4-Methoxybenzyl (cyclohexyl)oxoacetate (12)

The synthesis was carried out as described above under k), using 6.62 g (35.9 mmol) of ethyl (cyclohexyl) oxoacetate, 6.06 g (43.9 mmol) of 4-methoxybenzyl alcohol, 0.5 ml of $NaOCH_3$ (30% in methanol) and 50 ml of cyclohexane. Column chromatography ($SiO_2$, heptane/ether 7:3) afforded one fraction of the pure product together with another fraction of lower purity. The latter was rechromatographed ($SiO_2$, heptane/ether 8:2) to yield a total of 1.15 g (12%) of pure product as a slightly yellow oil.

UV/Vis (hexane): 395 (sh, 5); 375 (sh, 15); 367 (sh, 18); 360 (sh, 21); 352 (sh, 24); 337 (26); 324 (sh, 25); 312 (sh, 24); 288 (sh, 230); 280 (1520); 274 (1790); 268 (sh, 1590); 265 (sh, 1520); 259 (sh, 1170).

IR (neat): 3001w, 2929m, 2853m, 1806w, 1721s, 1612m, 1586m, 1514s, 1461m, 1449m, 1424w, 1369w, 1303m, 1271m, 1246s, 1225s, 1174s, 1138s, 1112m, 1080m, 1063s, 1031s, 996s, 984s, 946w, 916w, 895m, 849w, 821s, 755w, 719w.

¹H NMR (360 MHz, $CDCl_3$): 7.38-7.30 (m, 2 H); 6.94-6.85 (m, 2 H); 5.21 (s, 2 H); 3.81 (s, 3 H); 3.08-2.94 (m, 1 H); 1.98-1.83 (m, 2 H); 1.83-1.71 (m, 2 H); 1.71-1.56 (m, 1 H); 1.41-1.0 (m, 5 H).

¹³C NMR (90.6 MHz, $CDCl_3$): 197.39 (s); 161.94 (s); 160.04 (s); 130.51 (d); 126.81 (s); 114.08 (d); 67.58 (t); 55.31 (q); 46.41 (d); 27.46 (t); 25.70 (t); 25.27 (t).

MS (EI): 276 (M⁺, 1); 135 (1); 123 (1); 122 (10); 121 (100); 111 (2); 107 (1); 106 (2); 94 (1); 92 (1); 91 (3); 90 (1); 89 (1); 83 (7); 78 (5); 77 (4); 65 (1); 55 (9); 53 (1); 52 (1); 51 (1); 41 (3); 39 (2).

n) 3-(4-tert-Butylphenyl)-2-methylpropyl cyclohexyl(oxo) acetate (13)

The synthesis was carried out as described above under k), using 4.8 g (26.1 mmol) of ethyl (cyclohexyl)oxoacetate, 4.0 g (21.5 mmol) of 3-(4-tert-butylphenyl)-2-methylpropanol (obtained by reduction of (±)-3-(4-tert-butylphenyl)-2-methylpropanal (Lilial®) with $LiAlH_4$ in ether), 0.5 ml of $NaOCH_3$ (30% in methanol) and 40 ml of cyclohexane. Column chromatography ($SiO_2$, heptane/ether 8:2) afforded 3.43 g (46%) of a colorless oil.

UV/Vis (hexane): 393 (sh, 4); 384 (sh, 7); 375 (sh, 12); 366 (sh, 15); 357 (sh, 18); 351 (sh, 20); 336 (22); 322 (sh, 20); 271 (270); 263 (330); 257 (280); 251 (240); 244 (sh, 240).

IR (neat): 3089w, 3055w, 3021w, 2953m, 2928m, 2855m, 1723s, 1512m, 1450m, 1410w, 1387w, 1364w, 1310w, 1270m, 1226m, 1183w, 1139m, 1112w, 1079m, 1064m, 998m, 963w, 954w, 919w, 892w, 843w, 800w, 718w, 674w.

$^1$H NMR (360 MHz, CDCl$_3$): 7.35-7.27 (m, 2 H); 7.12-7.05 (m, 2 H); 4.14 (ABX, J=10.7, 5.6, 1 H); 4.07 (ABX, J=10.7, 6.7, 1 H); 3.06-2.95 (m, 1 H); 2.70 (ABX, J=13.7, 6.5, 1 H); 2.48 (ABX, J=13.7, 7.7, 1 H); 2.28-2.12 (m, 1 H); 1.97-1.86 (m, 2 H); 1.86-1.74 (m, 2 H); 1.74-1.63 (m, 1 H); 1.45-115 (m, 5 H); 1.31 H); 0.98 (d, J=6.7, 3 H).

$^{13}$C NMR (90.6 MHz, CDCl$_3$): 197.52 (s); 162.24 (s); 149.01 (s); 136.34 (s); 128.75 (d); 125.27 (d); 70.11 (t); 46.44 (d); 39.08 (t); 34.43 (d); 34.38 (s); 31.39 (q); 27.44 (t); 25.71 (t); 25.30 (t); 16.77 (q).

MS (EI): 345 ([M+H]$^+$, 1); 344 (M$^{+,\ 6}$); 330 (1); 329 (6); 234 (9); 233 (52); 231 (4); 217 (2); 190 (1); 189 (10); 188 (27); 178 (2); 177 (13); 175 (2); 174 (7); 173 (31); 161 (1); 160 (1); 159 (5); 148 (6); 147 (45); 146 (1); 145 (8); 133 (3); 132 (23); 131 (29); 130(1); 129(2); 128(2); 127(1); 119(4); 118(3); 117(19); 116 (3); 115 (5); 112 (3); 111 (40); 110 (1); 105 (5); 104 (2); 103 (1); 91 (9); 84 (7); 83 (100); 81 (1); 79 (1); 77 (1); 67 (1); 65 (1); 57 (14); 55 (20); 54 (1); 53 (1); 41 (9); 39 (2); 29 (2).

o) (1R,3R,4S)-3-p-Menthanyl (cyclohexyl)oxoacetate (14)

The synthesis was carried out as described above under k), using 25.03 g (136 mmol) of ethyl (cyclohexyl) oxoacetate, 25.70 g (165 mmol) of (−)-menthol and 1 ml of NaOCH$_3$ (30% in methanol) in 150 ml of cyclohexane. Fractional distillation afforded 23.14 g (58%) of a colorless oil.

B.p. 122° C./0.33 mbar.

UV/Vis (hexane): 394 (sh, 5); 383 (sh, 8); 375 (sh, 12); 366 (sh, 16); 360 (sh, 18); 351 (sh, 20); 337 (22).

IR (neat): 2949m, 2928m, 2854m, 1717s, 1450m, 1387w, 1370m, 1332w, 1311w, 1274m, 1230m, 1181w, 1139m, 1111w, 1081m, 1064m, 1037w, 1027w, 1006w, 995s, 980m, 951 m, 912m, 894m, 869w, 844m, 802w, 787w, 717m.

$^1$H NMR (360 MHz, CDCl$_3$): 4.83 (td, J=10.9, 4.36, 1 H); 3.05-2.94 (m, 1 H); 2.08-1.99 (m, 1 H); 1.96-1.62 (m, 8 H); 1.59-1.45 (m, 2 H); 1.44-0.99 (m, 7 H); 0.93 (d, J =6.7, 3 H); 0.90 (d, J=7.1, 3 H); 0.77 (d, J=7.1,3 H).

$^{13}$C NMR (90.6 MHz, CDCl$_3$): 198.09 (s); 162.16 (s); 76.71 (d); 46.79 (d); 46.32 (d); 40.49 (t); 34.10 (t); 31.50 (d); 27.37 (t); 26.25 (d); 25.76 (t); 25.32 (t); 25.26 (t); 23.38 (t); 21.95 (q); 20.67 (q); 16.17 (q).

MS (EI): 294 (M$^+$, 1); 250 (1); 167 (1); 154 (4); 140 (4); 139 (33); 138 (8); 137 (1); 123 (2); 112 (1); 111 (9); 110 (1); 109 (1); 98 (1); 97 (16); 96 (1); 95 (5); 84 (7); 83 (100); 82 (2); 81 (12); 80 (1); 79 (2); 71 (3); 70 (1); 69 (19); 68 (1); 67 (5); 57 (13); 56 (2); 55 (33); 54 (2); 53 (2); 43 (5); 42 (1); 41 (11); 39 (2); 29 (2); 27 (1).

p) 2-Pentyl-1-cyclopentyl (cyclohexyl)oxoacetate (15)

The synthesis was carried out as described above under k), using 6.62 g (36 mmol) of ethyl (cyclohexyl)oxoacetate, 6.80 g (44 mmol) of 2-pentyl cyclopentanol and 1 ml of NaOCH$_3$ (30% in methanol) in 50 ml of cyclohexane for 24 h. Column chromatography (SiO$_2$, heptane/ether 8:2) afforded 5.91 g (55%) of a yellow oil (mixture of diastereoisomers). The UV/Vis spectrum indicated the presence of a colored impurity.

UV/Vis (hexane): 395 (sh, 4); 383 (sh, 7); 374 (sh, 11); 366 (sh, 14); 358 (sh, 16); 349 (sh, 19); 320 (sh, 23); 303 (sh, 34); 289 (sh, 43).

IR (neat): 2924m, 2853m, 1806w, 1719s, 1461w, 1449m, 1376w, 1311w, 1275m, 1254w, 1229m, 1183w, 1139m, 1116w, 1081m, 1064m, 1028w, 996m, 968w, 925w, 894w, 844w, 724w.

$^1$H NMR (360 MHz, CDCl$_3$): 5.35-5.28 (m, 1 H); 4.96-4.89 (m, 1 H); 3.05-2.88 (m, 2 H); 2.10-1.55 (m, 10 H); 1.53-1.10 (m, 13 H); 0.93-0.80 (m, 3 H).

$^{13}$C NMR (90.6 MHz, CDCl$_3$): 197.99 (s); 162.29 (s); 162.26 (s); 83.72 (d); 80.36 (d); 46.58 (d); 46.42 (d); 45.39 (d); 44.81 (d); 33.49 (t); 32.53 (t); 32.07 (t); 31.94 (t); 31.80 (t); 30.20 (t); 29.61 (t); 29.12 (t); 28.18 (t); 27.60 (t); 27.46 (t); 27.38 (t); 25.32 (t); 22.76 (t); 22.59 (t); 22.03 (t); 14.05 (q).

MS (EI): 167 (1); 140 (1); 139 (8); 138 (7); 123 (1); 112 (1); 111 (11); 110 (1); 109 (1); 98 (2); 97 (25); 96 (2); 95 (3); 84 (7); 83 (100); 82 (5); 81 (4); 79 (2); 71 (4); 70 (2); 69 (22); 68 (2); 67 (9); 66 (1); 65 (1); 57 (11); 56 (2); 55 (29); 54 (3); 53 (2); 43 (4); 42 (1); 41 (12); 39 (3); 29 (3); 27 (1).

q) 4-(1,1 -Dimethylpropyl)- 1-cyclohexyl (cyclohexyl) oxoacetate (16)

The synthesis was carried out as described above under k), using 6.62 g (36 mmol) of ethyl (cyclohexyl)oxoacetate, 7.40 g (43.5 mmol) of 4-(1,1-dimethylpropyl)-1-cyclohexanol and 1 ml of NaOCH$_3$ (30% in methanol) in 50 ml of cyclohexane. Column chromatography (SiO$_2$, heptane/ether 8:2) afforded 4.78 g (43%) of a slightly yellow oil as a mixture of cis/trans isomers (~38:62).

UV/Vis (hexane): 394 (sh, 4); 385 (sh, 7); 375 (sh, 12); 367 (sh, 15); 339 (sh, 35); 326 (40); 312 (sh, 38); 297 (sh, 34); 283 (33); 272 (sh, 36).

IR (neat): 2929s, 2855m, 1800w, 1719s, 1462w, 1448m, 1387w, 1377w, 1364w, 1323w, 1309w, 1274m, 1254w, 1228m, 1182w, 1160w, 1140m, 1108w, 1081mn, 1064m, 1047w, 1005w, 995s, 948w, 928w, 906w, 894w, 875w, 830w, 805w, 780w, 745w, 719w.

$^1$H NMR (360 MHz, CDCl$_3$): 5.21-5.14 (m, 1 H (cis)); 4.85-4.72 (tt, J=11.3, 4.6, 1 H (trans)); 3.07-2.91 (m, 1 H); 2.17-1.04 (m, 21 H); 0.83-0.77 (m, 9 H).

$^{13}$C NMR (90.6 MHz, CDCl$_3$): 198.07 (s); 161.85 (s); 76.16 (d); 72.28 (d); 46.81 (d); 46.35 (d); 44.58 (d); 44.21 (d); 34.82 (s); 34.60 (s); 32.75 (t); 32.49 (t); 31.90 (t); 30.49 (t); 27.47 (t); 25.75 (t); 25.38 (t); 25.31 (t); 24.97 (t); 24.27 (q); 24.17 (q); 21.22 (t); 8.10 (q).

MS (EI): 264 (1); 193 (1); 181 (1); 153 (4); 152 (3); 137 (4); 124 (1); 6); 112 (1); 111 (14); 110 (2); 109 (1); 98 (4); 97 (55); 95 (5); 85 (2); 84 (4); 83 (60); 81 (12); 80 (1); 79 (2); 72 (6); 71 (100); 69 (13); 68 (1); 67 (11); 57 (15); 56 (3); 55 (51); 54 (4); 53 (3); 43 (32); 41 (22); 39 (4); 29 (7); 27 (4).

r) 1-(2-Naphthalenyl)ethyl (cyclohexyl)oxoacetate (17)

The synthesis was carried out as described above under k), using 6.62 g (24 mmol) of ethyl (cyclohexyl)oxoacetate, 7.5 g (29 mmol) of 1-(2-naphthalenyl)ethanol and 1 ml of NaOCH, (30% in methanol) in 70 ml of cyclohexane for 28 h. Column chromatography (SiO$_2$, heptane/ether 8:2) afforded 2.67 g of a colorless oil still containing about 30% of ethyl (cyclohexyl)oxoacetate.

$^1$H NMR (360 MHz, CDCl$_3$): 7.88-7.78 (m, 4 H); 7.54-7.44 (m, 3 H); 6.16 (q, J=6.6, 1 H); 3.08-2.93 (m, 1 H); 1.97-1.60 (m, 5 H); 1.72 (d, J=6.7, 3 H); 1.44-1.12 (m, 5 H).

$^{13}$C NMR (90.6 MHz, CDCl$_3$): 197.53 (s); 161.49 (s); 137.73 (s); 133.21 (s); 133.13 (s); 128.60 (d); 128.09 (d); 127.71 (d); 126.40 (d); 126.34 (d); 125.38 (d); 123.85 (d); 74.76 (d); 46.41 (d); 27.38 (t); 25.70 (t); 25.26 (t); 22.08 (q).

MS (EI): 310 (M$^+$, 1); 157 (2); 156 (14); 155 (100); 154 (22); 153 (16); 152 (8); 151 (2); 141 (2); 139 (1); 129 (3); 128 (9); 127 (9); 126 (2); 115 (4); 111 (3); 101 (1); 84 (1);

83 (17); 77 (4); 76 (4); 75 (2); 64 (1); 63 (2); 56 (1); 55 (16); 51 (2); 50 (1); 43 (2); 41 (9); 39 (4); 29 (3); 27 (3).

s) 3,7-Dimethyl-6-octenyl (cyclopentyl)oxoacetate (18)

In the first step, ethyl (cyclopentyl)oxoacetate was prepared as follows. A Grignard reagent prepared from 64.0 g of freshly distilled bromocyclopentane (0.43 mol) and 11.0 g of magnesium (0.45 mol) in 360 ml of dry ether and filtered under $N_2$ was added dropwise to a stirred solution of 48.2 g (0.33 mol) of diethyl oxalate in 300 ml of dry ether at −40° C. The mixture was slowly warmed to 0° C. and poured onto a sat. solution of $NH_4Cl$, extracted with ether and washed with water (pH~7). The organic phase was dried over $Na_2SO_4$ and concentrated. Fractional distillation gave 27.1 g (48%) of a colorless oil in sufficient purity for further derivatization. Column chromatography ($SiO_2$, heptane/ether 8:2) of 2.50 g afforded 2.04 g of product at high purity.

B.p. 42° C./0.1 mbar.

UV/Vis (hexane): 389 (sh, 3); 371 (sh, 9); 359 (sh, 13); 345 (sh, 15); 336 (15).

IR (neat): 3483w, 2956m, 2869m, 1723s, 1684m, 1469w, 1449m, 1399w, 1372w, 1318w, 1296m, 1254s, 1194m, 1159m, 1140m, 1091s, 1043s, 1029s, 952m, 906m, 858m, 780m, 708w.

$^1$H NMR (360 MHz, $CDCl_3$): 4.32 (q, J=7.1, 2 H); 3.56-3.44 (m, 1 H); 1.98-1.75 (m, 4 H); 1.75-1.57 (m, 4 H); 1.37 (t,J=7.1, 3 H).

$^{13}$C NMR (90.6 MHz, $CDCl_3$): 196.73 (s); 161.98 (s); 62.24 (t); 47.42 (d); 28.32 (t); 26.05 (t); 14.05 (q).

MS (EI): 170 (M$^+$, 5); 114 (1); 101 (1); 98 (4); 97 (48); 96 (4); 95 (1); 70 (6); 69 (100); 68 (3); 67 (6); 66 (1); 65 (1); 55 (4); 54 (1); 53 (2); 51 (1); 43 (1); 42 (2); 41 (22); 40 (2); 39 (7); 29 (5); 28 (1); 27 (4).

3,7-Dimethyl-6-octenyl (cyclopentyl)oxoacetate (18)

The synthesis was carried out as described above under k), using 6.07 g (35.6 mmol) of the product obtained above, 6.80 g (43.6 mmol) of citronellol and 0.5 ml of $NaOCH_3$ (30% in methanol) in 50 ml of cyclohexane. Column chromatography ($SiO_2$, heptane/ether 7:3) afforded 5.28 g (53%) of a yellow oil.

UV/Vis (hexane): 389 (sh, 4); 366 (sh, 12); 345 (sh, 17); 336 (17).

IR (neat): 3493w, 2957m, 2916m, 2869m, 1798w, 1724s, 1687m, 1451m, 1377m, 1354w, 1259m, 1190m, 1164m, 1144m, 1091m, 1047m, 1027m, 984w, 945m, 829m, 782w, 739w, 717w.

$^1$H NMR (360 MHz, $CDCl_3$): 5.13-5.03 (m, 1 H); 4.40-4.20 (m, 2 H); 3.54-3.42 (m, 1 H); 2.10-1.71 (m, 7 H); 1.71-1.45 (m, 6 H); 1.68 (s, 3 H); 1.60 (s, 3 H); 1.43-1.30 (m, 1 H); 1.29-1.13 (m, 1 H); 0.94 (d, J=6.3, 3 H).

$^{13}$C NMR (90.6 MHz, $CDCl_3$): 196.66 (s); 162.11 (s); 131.51 (s); 124.40 (d); 64.75 (t); 47.48 (d); 36.90 (t); 35.22 (t); 29.40 (d); 28.27 (t); 26.05 (t); 25.71 (q); 25.35 (t); 19.35 (q); 17.66 (q).

MS (EI): 280 (M$^+$, 1); 262 (2); 252 (1); 184 (1); 183 (6); 165 (1); 155 (3); 142 (1); 139 (2); 138 (20); 137 (6); 126 (1); 125 (1); 124 (2); 111 (1); 110 (2); 109 (9); 98 (1); 97 (39); 96 (7); 95 (21); 81 (23); 80 (2); 79 (1); 70 (7); 69 (100); 68 (5); 67 (9); (10); 54 (1); 53 (3); 43 (2); 42 (2); 41 (25); 40 (1); 39 (4); 29 (2); 27 (2).

t) (E)-3,7-Dimethyl-2,6-octadienyl 3-methyl-2-oxopentanoate (19)

The synthesis was caried out as described above under a), using 4.85 g (38 mmol) of 3-methyl-2-oxo pentanoic acid and 11.5 g (75 mmol) of geraniol in 130 ml of toluene for 24 h. Column chromatography ($SiO_2$, heptane/EtOAc 95:5) afforded 7.68 g of crude product, which was fractionally distilled to give 4.04 g (40%) of a colorless oil.

B.p. 82° C./0.2 mbar.

UV/Vis (hexane): 393 (sh, 5); 382 (sh, 9); 374 (sh, 13); 364 (sh, 17); 357 (sh, 19); 350 (sh, 21); 335 (23).

IR (neat): 2966m, 2929m, 2878m, 1746m, 1723s, 1670w, 1454m, 1377m, 1338w, 1274m, 1244m, 1163m, 1107m, 1085w, 1039s, 999m, 959m, 913m, 827w, 796w, 772w, 742w, 705w.

$^1$H NMR (360 MHz, $CDCl_3$): 5.46-5.35 (m, 1 H); 5.14-5.04 (m, 2 H); 4.77 (d, J=7.1, 2 H); 3.20-3.07 (m, 1 H); 2.20-2.00 (m, 4 H); 1.83-1.66 (m, 1 H); 1.74 (s, 3 H); 1.68 (s, 3 H); 1.60 (s, 3 H); 1.52-1.36 (m, 1 H); 1.13 (d, J=7.1, 3 H); 0.92 (t, J=7.5, 3 H).

$^{13}$C NMR (90.6 MHz, $CDCl_3$): 198.29 (s); 162.10 (s); 144.01 (s); 131.97 (s); 123.58 (d); 117.13 (d); 62.94 (t); 43.66 (d); 39.53 (t); 26.22 (t); 25.66 (q); 24.92 (t); 17.69 (q); 16.57 (q); 14.46 (q); 11.35 (q).

MS (EI): 266 (M$^+$, 1); 181 (1); 179 (1); 153 (1); 138 (3); 137 (28); 136 (6); 135 (5); 123 (1); 122 (1); 121 (2); 109 (1); 107 82); 96 (2); 95 (10); 94 (2); 93 (6); 92 (2); 91 (3); 85 (9); 83 (1); 82 (4); 81 (52); 80 (2); 79 (3); 78 (1); 77 (3); 71 (1); 70 (6); 69 (100); 68 (12); 67 (12); 66 (1); 65 (2); 58 (2); 57 (30); 56 (1); 55 (5); 54 (1); 53 (6); 51 (1); 43 (1); 42 (2); 41 (26); 40 (2); 39 (5) 29 (5); 28 (1); 27 (2).

u) 3,7-Dimethyl-6-octenyl (bicyclo[2.2.1]hept-2-yl)oxoacetate (20)

A Grignard reagent prepared from 4.00 g of 2-norbornyl bromide (23 mmol) and 0.59 g of magnesium (24 mmol) in 30 ml THF was, after filtration under $N_2$, added dropwise (during 45 min) to a stirred solution of 3.00 g (8 mmol) of bis(3,7-dimethyl-6-octenyl) oxalate in 40 ml of THF at −40° C. The mixture was slowly warmed to 0° C., quenched with 30 ml of a sat. solution of $NH_4Cl$. The reaction mixture was extracted with diethyl ether and water (2x) and the organic phase dried over $Na_2SO_4$. Repetitive column chromatography ($SiO_2$, heptane/ether 9:1 and heptane/ether 95:5) followed by MPLC on a Lobar column ($SiO_2$ Merck, heptane/ether 85:15) finally afforded 0.188 g (3%) of the pure product as a colorless oil.

$^1$H NMR (360 MHz, $CDCl_3$): 5.13-5.04 (m, I H); 4.37-4.22 (m, 2 H); 3.06 (m, 1 H); 2.59-2.48 (m, 1 H); 2.36-2.27 (m, 1 H); 2.09-1.84 (m, 3 H); 1.84-1.69 (m, 1 H); 1.68 (s, 3 H); 1.66-1.45 (m, 4 H); 1.60 (s, 3 H); 1.45-1.30 (m, 3 H); 1.30-108 (m, 4H); 0.94(d,J=6.3, 3 H).

$^{13}$C NMR (90.6 MHz, $CDCl_3$): 195.33 (s); 162.08 (s); 131.50 (s); 124.39 (d); 64.75 (t); 50.37 (d); 39.82 (d); 36.91 (t); 36.28 (d); 35.84 (t); 35.23 (t); 31.86 (t); 29.64 (t); 29.43 (d); 28.78 (t); 25.71 (q); 25.36 (t); 19.34 (q); 17.66 (q).

MS (EI): 288 (1); 183 (4); 168 (1); 155 (1); 139 (2); 138 (15); 137 (2); 124 (3); 123 (30); 122 (2); 121 (1); 110 (1); 109 (5); 97 (1); 96 (11); 95 (100); 93 (4); 91 (1); 83 (4); 82 (19); 81 (21); 80 (5); 79 (3); 77 (2); 70 (2); 69 (23); 68 (5); 67 (22); 66 (3); 65 (3); 57 (3); 56 (3); 55 (15); 54 (2); 53 (5); 43 (4); 42 (3); 41 (33); 39 (6); 29 (5); 28 (1); 27 (5).

EXAMPLE 2

Release of fragrant aldehydes and ketones from various citronellyl α-keto esters in solution or in the neat state 0.01 M solutions (5 ml) of the α-keto esters prepared as described in example 1, in toluene, acetonitrile or isopropanol, were prepared and irradiated with a xenon or a UV lamp or exposed to outdoor sunlight in 10 ml volumetric flasks. Samples in the neat state were also irradiated under the same conditions. Before irradiation in solution, 1 ml of a 0.01 M solution of decanol was added which served as internal standard for GC analysis. The results are found in the Table I below. Table I indicates the amount of released aldehyde or ketone in mol%, the amount of remaining starting material is indicated in brackets. It was also observed that olefins were released, from compounds (7) and (8) of example 1, together with release of citronellal.

TABLE 1

Results of the photoirradiations of different α-keto esters in solution and in their neat state

| Structure of Compounds | N° | Light Source | Toluene 3 h | | 2-Propanol 3 h | | Acetonitrile 3 h | | Neat 3.5 h | |
|---|---|---|---|---|---|---|---|---|---|---|
| 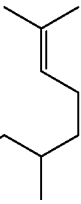 | 1 | Xenon<br>UV<br>sunlight | 27<br>44 | (10)<br>(<5) | 5 | (65) | 29<br>30 | (15)<br>(45) | | |
| 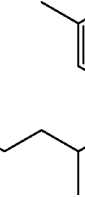 | 2 | Xenon<br>UV<br>sunlight | 33<br>50 | (<5)<br>(<5) | 11 | (40) | 27<br>29 | (5)<br>(15) | | |
| 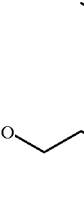 | 3 | Xenon<br>UV<br>sunlight | 55<br>19<br>23 | (<5)[b]<br>(60)<br>(<5) | 5<br>30 | (85)<br>(20) | 36<br>14<br>15 | (<5)[b]<br>(65)<br>(<5) | 5<br><1 | (40)<br>(55) |
| 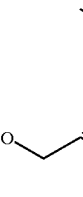 | 19 | Xenon<br>UV<br>sunlight | 15/26[f]<br>17/21[f] | (<5)<br>(20) | 6/26[f]<br>6/34[f] | (20)<br>(20) | 7/12[f]<br>7/11[f] | (20)<br>(35) | 0 | (35) |
| 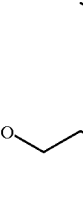 | 4 | Xenon<br>UV<br>sunlight | 38<br>13<br>21 | (<5)[b]<br>(75)<br>(<5) | 9<br>13 | (45)<br>(20) | 31<br>7<br>21 | (10)[b]<br>(95)<br>(<5) | 1<br>0 | (45)<br>(55) |

TABLE 1-continued

Results of the photoirradiations of different α-keto esters in solution and in their neat state

| Structure of Compounds | N° | Light Source | Toluene 3 h | | 2-Propanol 3 h | | Acetonitrile 3 h | | Neat 3.5 h | |
|---|---|---|---|---|---|---|---|---|---|---|
|  | 7 | Xenon<br>UV<br>sunlight | 11<br>2/6[d] | (30)[b]<br>(85) | 0/3[d] | (—)[c] | 1/6[d] | (80) | 2/11[d] | (30) |
|  | 8 | Xenon<br>UV<br>sunlight | 8<br>0/5[e]<br>7/42[e] | (50)[b]<br>(85)<br>(35) | 0/5[e]<br>3/21[e] | (70)<br>(55) | 0/5[e]<br>0/37[e] | (95)<br>(25) | 1/10[e]<br>0/6[e] | (35)<br>(75) |
|  | 18 | Xenon<br>UV<br>sunlight | 24<br>37 | (<5)<br>(<5) | 17 | (15) | 20<br>22 | (5)<br>(15) | | |
|  | 20 | Xenon<br>UV<br>sunlight | 26 | (10) | | | | | | |
|  | 9 | Xenon<br>UV<br>sunlight | ≈45<br>25<br>38 | (<5)[b]<br>(65)<br>(<5) | 9<br>35 | (90)<br>(15) | 13<br>18 | (70)<br>(<5) | 3<br><1 | (35)<br>(45)[b] |

TABLE 1-continued

Results of the photoirradiations of different α-keto esters in solution and in their neat state

| Structure of Compounds | N° | Light Source | Toluene 3 h | | 2-Propanol 3 h | | Acetonitrile 3 h | | Neat 3.5 h | |
|---|---|---|---|---|---|---|---|---|---|---|
| (cyclohexyl α-keto ester of geraniol) | 10 | Xenon<br>UV<br>sunlight | 26/43[f]<br>19/25[f] | (<5)<br>(5) | 10/33[f]<br>10/48[f] | (30)<br>(30) | 11/19[f]<br>11/17[f] | (20)<br>(30) | <1/0[f] | (50) |
| (cyclohexyl α-keto ester of long-chain alcohol) | 11 | Xenon<br>UV<br>sunlight | 52<br>52 | (0)<br>(<5) | 28<br>26 | (5)<br>(5) | 27<br>25 | (<5)<br>(<5) | 5<br>4 | (45)<br>(55) |
| (cyclohexyl α-keto ester of p-methoxybenzyl alcohol) | 12 | Xenon<br>UV<br>sunlight | 81<br>86 | (<5)<br>(<5) | 20 | (25)[c] | 66 | (30) | | |
| (cyclohexyl α-keto ester of p-t-butylbenzyl-methylpropanol) | 13 | Xenon<br>UV<br>sunlight | 69<br>63 | (<5)<br>(<5) | 49 | (15) | 52<br>53 | (<5)<br>(5) | | |
| (cyclohexyl α-keto ester of menthol) | 14 | Xenon<br>UV<br>sunlight | quant.<br>quant. | (<5)<br>(10) | 53<br>44 | (10)<br>(10) | 91<br>86 | (<5)<br>(5) | 75<br>21 | (40)<br>(50) |
| (cyclohexyl α-keto ester of hexylcyclopentanol) | 15 | Xenon<br>UV<br>sunlight | 76 | (<5) | 53 | (15) | 75<br>73 | (<5)<br>(10) | | |

TABLE 1-continued

Results of the photoirradiations of different α-keto esters in solution and in their neat state

| Structure of Compounds | N° | Light Source | Toluene 3 h | | 2-Propanol 3 h | | Acetonitrile 3 h | | Neat 3.5 h | |
|---|---|---|---|---|---|---|---|---|---|---|
| 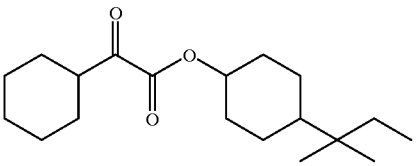 | 16 | Xenon<br>UV<br>sunlight | 93<br>93 | (<5)<br>(<5) | 65 | (20) | 88<br>83 | (10)<br>(5) | | |
| 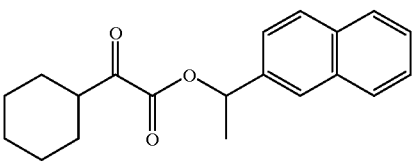 | 17 | Xenon<br>UV<br>sunlight | | | 14 | (55)ᶜ | 6 | (90) | | |
| 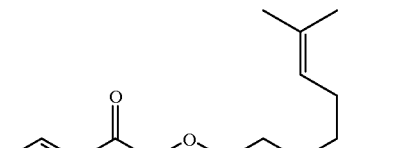 | 5 | Xenon<br>UV<br>sunlight | 33<br>13<br>27 | (10)ᵇ<br>(65)<br>(<5) | 4<br>6 | (50)<br>(30) | 16<br>7<br>15 | (15)ᵇ<br>(80)<br>(20) | <1<br>0 | (<5)<br>(<5) |
| 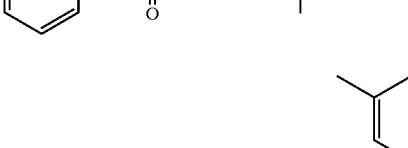 | 6 | Xenon<br>UV<br>sunlight | 9<br>4 | (20)ᵇ<br>(55) | | | 2 | (45) | <1 | (<5) |

All numbers are average values of 2 or 3 samples.
ᵃamount of remaining starting material rounded to ±5%,
ᵇamount of starting material estimated from blank sample,
ᶜyield not or only approximatively determined due to transesterification,
ᵈmol-% of citronellal/dodecene liberated by hydrogen abstraction from the alkyl chain,
ᵉmol-% of citronellal/tridecene liberated by hydrogen abstraction of the alkyl chain,
ᶠmol-% of trans/cis citral.

EXAMPLE 3
Release of citronellal from various citronellyl α-keto esters in after-shave lotions Compounds (3) and (4) of example 1 were each dissolved in an amount of 0.29 g in 19.54 g of a standard after-shave lotion base, under addition of a standard solubilizer (Cremophor RH40, BASF AG). For each of the compounds, three samples of 6 ml (one of which was wrapped in aluminium foil to serve as reference) were irradiated in 10 ml volumetric flasks for 3 h with a xenon lamp. The irradiated samples were analyzed by HPLC using citronellal and the corresponding starting materials as external standards. The reference experiment (aluminium foil wrapped) showed no release of citronellal. The results obtained with the other samples are summarized in Table 2.

TABLE 2

Results of the photoirradiations of α-keto esters in after-shave lotion

| Compound N° | mol-% of citronellal liberated | mol-% of remaining* starting material |
|---|---|---|
| 3 | 12 | 36 |
| 4 | 2 | 53 |

*average of 2 samples

EXAMPLE 4
Release of citronellal or menthone from various citronellyl α-keto esters in a window cleaner and in an all-purpose cleaner 10–15 mg of the respective α-keto ester as specified in Table 3 below were weighed into 10 ml volumetric flasks. A solubilizer was added (Cremophor RH40, BASF AG for window cleaner, Triton X100 (Rohm & Haas) for all-purpose cleaner), before adding 6 ml of the respective base, i.e. a standard type window cleaner, or a Fabuloso® (registered trademark of Colgate-Palmolive, USA) type all-purpose cleaner, and agitating until the solution became clear. For each irradiation series four samples were prepared for each compound, one of which, wrapped in aluminium foil, served as reference. All the samples were irradiated for 3, 6, or 15 h with either the Xenon or the UV lamp or exposed to outdoor sunlight. In all cases the formation of citronellal or menthone could be smelled after the photolysis. In order to quantify the amount of aldehyde or ketone (and of the remaining starting material) in the application base, the irradiated samples were subjected to GC analysis (extraction and on-column injection).

For analysis, 1 g of NaCl was added and the samples were extracted with 3 ml of a 0.35 mM (50 mg/l) solution of undecane (used as internal standard) in iso-octane. The aqueous layer was re-extracted with 2 ml of the iso-octane solution and the two organic phases were combined and injected directly onto a GC column. The results obtained for the different bases are summarized in Table 3.

TABLE 3

Results of the photoirradiations of different α-keto esters in different household application bases

| Structures of Compounds | N° | Tested Application | Light Source | Irradiation Time | Yield of Perfume[a] in mol-% | Remaining Starting Material in mol-% |
|---|---|---|---|---|---|---|
| 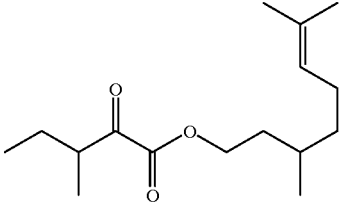 | 3 | Window Cleaner (solution) | Xenon | 3 h | 8 | (50) |
| | | | | 6 h | 3 | (10) |
| | | | UV | 3 h | 2 | (90) |
| | | | | 6 h | 3 | (70) |
| | | | | 15 h | 6 | (60) |
| | | | Sun | 3 h | 3 | (90) |
| | | | | 6h | 2 | (40) |
| | | Fabuloso ® (solution) | Xenon | 3 h | 6 | (25) |
| | | | | 6 h | 2 | (5) |
| | | | UV | 3 h | 3 | (85) |
| | | | | 15 h | 10 | (45) |
| | | | Sun | 3 h | <1 | (60) |
| | | | | 6h | <1 | (30) |
| 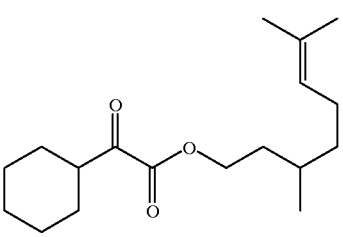 | 9 | Window Cleaner (solution) | Xenon | 3 h | 3 | (15) |
| | | | | 6 h | 6 | (20) |
| | | | UV | 3 h | 3 | (80) |
| | | | | 6 h | 3 | (70) |
| | | | | 15 h | 6 | (35) |
| | | | Sun | 3 h | 8 | (75) |
| | | Fabuloso ® (solution) | Xenon | 3 h | 1 | (25) |
| | | | | 6 h | <1 | (10) |
| | | | UV | 3 h | 1 | (85) |
| | | | | 15 h | 15 | (45) |
| | | | Sun | 3 h | <1 | (50) |
| 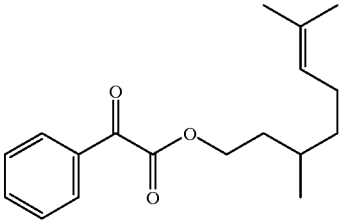 | 5 | Window Cleaner (solution) | UV | 3 h | 1 | (40) |

TABLE 3-continued

Results of the photoirradiations of different α-keto esters in different household application bases

| Structures of Compounds | N° | Tested Application | Light Source | Irradiation Time | Yield of Perfume[a] in mol-% | Remaining Starting Material in mol-% |
|---|---|---|---|---|---|---|
| 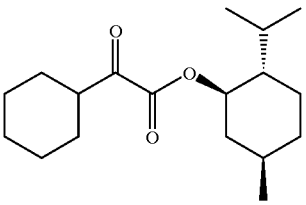 | 14 | Window Cleaner (solution) | Xenon | 3 h | 26 | (40) |
| | | | | 6 h | 22 | (25) |
| | | | Sun | 3 h | 28 | (80) |
| | | | | 6 h | 37 | (75) |
| | | Fabuloso® (solution) | Xenon | 3 h | 37 | (35) |
| | | | | 6 h | 15 | (20) |
| | | | Sun | 3 h | 36 | (80) |
| | | | | 6 h | 32 | (50) |

All numbers are average values of 2 or 3 samples.
[a]citronellal was released from compounds 7, 13 and 9, respectively, menthone was liberated from compound 18.
[b]amount of remaining starting material rounded to ±5%.

EXAMPLE 5
Dynamic headspace analysis in all purpose cleaners (APC)

In order to follow the perfume release under more realistic application conditions, quantitative dynamic headspace analyses were carried out. The formation of citronellal from its precursor in an APC application was compared to the behaviour of free citronellal in the same base. Solutions of a base of the Fabuloso® type containing either 0.3 mass-% of citronellal precursor 9 or 0.3 mass-% of pure citronellal (~2 molar equivalents) were prepared and deposited in self-built 3.5 l Pyrex® glass containers covered with a thin window glass plate. The chambers were exposed to outdoor sunlight for 6 h and continuously flushed with an air stream. Every hour the volatiles contained in the air stream were adsorbed on a Tenax cartridge (during 15 min) and the light intensity was measured. The amount of citronellal trapped on the cartridges was desorbed and quantified by GC analysis and are summarized in Table 4.

The amount of citronellal released increases with increasing light intensity and decreases when the intensity decreases, with the maximum of release being obtained shortly after the maximum of irradiation was measured. The amount of free citronellal, however, was found to decrease steadily with increasing time and, no dependency on the light intensity was observed.

TABLE 4

Comparison of the dynamic headspace of free citronellal and citronellal released from precursor 9 in a Fabuloso ® type APC irradiated with outdoor sunlight.

| Time [h] | Free citronellal in base (0.3 mass-%) [ng $l^{-1}$] | Citronellal released from precursor 9 in base (0.3 mass-%) [ng $l^{-1}$] | Sunlight intensity [lux] |
|---|---|---|---|
| 1 | 154086 | 1579 | 38500 |
| 2 | 117735 | 4752 | 53500 |
| 3 | 67015 | 7475 | 64500 |
| 4 | 50632 | 7829 | 63000 |
| 5 | 33215 | 7297 | 52500 |
| 6 | 19757 | 5919 | 35000 |

The above described experiment was repeated using 0.3 mass-% of menthone precursor 14 or 0.15 mass-% of pure menthone (~1 molar equivalent) in an APC application of the Fabuloso® type. Again a dependency of perfume release of the irradiation intensity could be observed, see Table 5, whereas the amount of unprotected menthone decreased continuously over time. Working with molar equivalents instead of mass equivalents shows that the perfume concentration of both systems are in the same order of magnitude. At the beginning of the experiment the concentration of unprotected menthone is about three times stronger than the concentration of the perfume released from the precursor. At the end of the experiment the perfume released from the keto ester contributes more strongly than the free menthone.

TABLE 5

Comparison of the dynamic headspace of free menthone and menthone released from precursor 14 in a Fabuloso ® type APC irradiated with outdoor sunlight

| Time [h] | Free menthone in base (0.15 mass-%) [µg $l^{-1}$] | Menthone released from precursor 14 in base (0.3 mass-%) [µg $l^{-1}$] | Sunlight intensity [lux] |
|---|---|---|---|
| 0.5 | 94.6 | 33.1 | 53000 |
| 1.5 | 86.4 | 59.7 | 71000 |
| 2.5 | 81.5 | 70.0 | 86750 |
| 3.5 | 76.7 | 68.9 | 88500 |
| 4.5 | 64.2 | 63.3 | 80500 |
| 5.5 | 47.4 | 60.5 | 69250 |
| 6.5 | 39.1 | 48.1 | 53000 |

EXAMPLE 6
Dynamic headspace analysis for the slow release on hair

In order to test the performance of the controlled photochemical release of perfumes in typical body care applications, 0.2 mass-% of precursor 9 dissolved in a leave-in hair conditioner of the standard type was sprayed four times on a hair curl (~5 g weight) and irradiated in a glass tube for 3 h with a Xenon lamp. The hair curl had been washed beforehand with an unperfumed shampoo base and the amount of conditioner deposed on the hair was weighed precisely. A comparison experiment with 0.1 mass-% (~1 molar equivalent) of unprotected citronellal in the same base was carried out under identical conditions.

During irradiation, the glass tube was connected to a charcoal filter (for air decontamination) and a Tenax cartridge and continuously flushed with an air stream (80 ml/min, corresponding to 4 renewals of air/sampling). The diffusion of citronellal was monitored over a period of three hours and four samplings at t=0, 1, 2 and 3 h were carried out. At each sampling, the citronellal diffusing from the hair was adsorbed onto a Tenax cartridge during 15 min, respectively. The cartridges were then thermally desorbed and the concentration of citronellal precisely quantified by GC (Table 6).

TABLE 6

Comparison of the dynamic headspace of free citronellal and citronellal released from precursor 9 in a leave-in hair conditioner irradiated with a Xenon lamp.

| Time [h] | Free citronellal in hair conditioner (0.1 mass-%) [ng $l^{-1}$] | Citronellal released from precursor 9 in hair conditioner (0.2 mass-%) [ng $l^{-1}$] | Xenon light intensity [lux] |
|---|---|---|---|
| 0 | 20700 | 284 | 78000 |
| 1 | 435 | 394 | 86000 |
| 2 | 127 | 237 | 86500 |
| 3 | 39 | 151 | 87500 |

Table 6 illustrates that the concentration of unprotected citronellal decreases rapidly with time whereas the citronellal released from the precursor remains almost constant during the experiment with constant light intensity. After only one hour of irradiation the concentration of citronellal released from the precursor is as high as the concentration of the unprotected aldehyde, and thereafter remains higher than the concentration of the unprotected aldehyde.

EXAMPLE 7

Dynamic headspace analysis for the slow release on cotton fabric

The release of citronellal from precursor 9 was compared to the diffusion of unprotected aldehyde on cotton fabric. For the study, precisely determined amounts of ethanolic solutions containing either 0.2 mass-% of 9 or 0.1 mass-% (~1 molar equivalent) of unprotected citronellal, respectively, were sprayed four times on 4 ×20 cm cotton sheets, which had been washed beforehand with an unperfumed detergent base. The irradiation was carried out in a Pyrex® glass tube for 3 h with a Xenon lamp as described above.

Again a rapid decrease of the released amount unprotected citronellal over time was observed, whereas the release of citronellal from the precursor remained constant with respect to the irradiation intensity, as illustrated in Table 7. The light dependence of the controlled perfume release was verified in a blank experiment. After only 3 h of irradiation comparable concentrations of citronellal were obtained either from the experiment with the free perfume or from release of the precursor compound.

TABLE 7

Comparison of the dynamic headspace of free citronellal and citronellal released from precursor 9 on cotton sheets irradiated with a Xenon lamp.

| Time [h] | Free citronellal on cotton (0.1 mass-% in EtOH) [ng $l^{-1}$] | Citronellal released from precursor 9 on cotton (0.2 mass-% in EtOH) [ng $l^{-1}$] | Xenon light intensity [lux] |
|---|---|---|---|
| 0–0.25 | 3022 | 71 | 92500 |
| 1–1.25 | 1590 | 168 | 89250 |

TABLE 7-continued

Comparison of the dynamic headspace of free citronellal and citronellal released from precursor 9 on cotton sheets irradiated with a Xenon lamp.

| Time [h] | Free citronellal on cotton (0.1 mass-% in EtOH) [ng $l^{-1}$] | Citronellal released from precursor 9 on cotton (0.2 mass-% in EtOH) [ng $l^{-1}$] | Xenon light intensity [lux] |
|---|---|---|---|
| 2–2.25 | 469 | 150 | 80750 |
| 3–3.25 | 116 | 115 | 81750 |

EXAMPLE 8

Slow release from cotton sheets treated with fabric softener

In a typical experiment, ten cotton towels were washed with an unperfumed, lipase free detergent powder and a fabric softener containing either 0.8 mass-% of keto ester 9 or 0.23 equivalents of the theoretically releasable unprotected aldehyde, respectively. The towels were washed at 40° C. without prewashing cycle and dried in the dark overnight. Two towels of each type were irradiated with the above described UV lamp in one covered Pyrex® crystallizing dish with an approximative volume of 3.5 l and compared to a set of non irradiated samples. After 3 h of irradiation the towels were analyzed by nine panelists. In all cases the irradiated towels with precursor 9 were characterized to give a fresh, floral, citrus type odor, and the average intensity was given the value 3 on an increasing scale starting at 0 and ending at 10. In the case of the unprotected citronellal or the two blank samples, the panelists detected only a weak odor with an intensity of 1 on the scale from 0 to 10.

The photoperfume precursor can therefore sucessfully be deposed on fabrics in a normal washing cycle, and the release of the desired perfume is detected in perceptible amounts upon irradiation of the dry fabric.

EXAMPLE 9

Release of menthone from an all-purpose cleaner

An all-purpose cleaner of the Fabuloso® type containing 0.3% of the compound 14 was prepared. This cleaner and the same cleaner without any perfume were placed into trapezoid flashes which were exposed to sunlight for 3 h (see also Example 4). The thus-obtained samples were then compared on a blind test by a panel of 15 non-experts. When the sample containing the photoperfume was the odd sample, 14 of the panelists correctly distinguished the samples. When the odd sample was the one containing the unperfumed base, 13 of the panelists correctly attributed the samples.

EXAMPLE 10

Release of menthone from a window cleaner

A window cleaner of the type described in Example 11 containing 0.3% of the compound 14 was prepared. This cleaner and the same cleaner without any perfume were placed into trapezoid flashes which were exposed to sunlight for 3 h. The thus-obtained samples were then compared on a blind test by a panel of 15 non-experts. When the sample containing the photoperfume was the odd sample, 12 of the panelists correctly distinguished the samples. When the odd sample was the one containing the unperfumed base, 10 of the panelists correctly attributed the samples.

What is claimed is:

1. An α-keto ester of formula

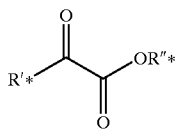 (I)

in which
a) R'* is a phenyl, cyclohexyl or cyclopentyl group, or a linear or branched alkyl group from $C_1$ to $C_4$, with the exception of a n-butyl group; and
b) R"* is the organic part of a primary or secondary alcohol R"*OH from which is derived a fragrant aldehyde or ketone;
and provided that at least one of the groups R'* and R"* is a group derived from a fragrant compound;

provided that R'* is not a methyl group,

R"* is not a menthyl or a benzyl group, and that (−)-(1S,1R)-1,7,7-trimethylbicyclo[2.2.1]heptan-2-yl (4-methylphenyl)oxoacetate and hexyl (cyclohexyl) oxoacetate are excluded.

2. The α-keto ester according to claim 1, wherein the fragrant aldehyde or ketone from which is derived the primary or secondary alcohol from which the organic part R"* is present in the α-keto ester as defined in formula (I) is citronellal, citral, hydroxycitronellal, methyl dihydrojasmonate, 4-(4-hydroxy-1-phenyl)-2-butanone, anisaldehyde, menthone, 2-pentyl-1-cyclopentanone, 4-(1,1-dimethylpropyl)-1-cyclohexanone, 2-naphtalenyl-1-ethanone, or a saturated, unsaturated, linear or branched aldehyde from $C_6$ to $C_{13}$.

* * * * *

UNITED STATES PATENT AND TRADEMARK OFFICE
CERTIFICATE OF CORRECTION

PATENT NO. : 6,492,323 B2  
APPLICATION NO. : 09/794694  
DATED : December 10, 2002  
INVENTOR(S) : Herrmann Page 1 of 1

It is certified that error appears in the above-identified patent and that said Letters Patent is hereby corrected as shown below:

Title Page:
"(*) Notice:" change "10 days" to --0 days--.

Column 36:
Line 13, after "dihydrojasmonate," insert --{3-(4-tert-butylphenyl)-2-methylpropanal},--.

Signed and Sealed this

Tenth Day of July, 2007

JON W. DUDAS  
*Director of the United States Patent and Trademark Office*